(12) United States Patent
Park et al.

(10) Patent No.: US 8,956,737 B2
(45) Date of Patent: Feb. 17, 2015

(54) RED PHOSPHORESCENT COMPOUND AND ORGANIC ELECTROLUMINESCENT DEVICE USING THE SAME

(75) Inventors: Chun Gun Park, Gwanak-gu (KR); Jung Keun Kim, Seoul (KR); Hyun Cheol Jeong, Gyeongsangnam-do (KR); Jong Kwan Bin, Gyeonggi-do (KR); Sung Hoon Pieh, Seoul (KR); Do Han Kim, Seoul (KR); Yong Kwan Kim, Choongcheongbuk-do (KR)

(73) Assignee: LG Display Co., Ltd., Seoul (KR)

( * ) Notice: Subject to any disclaimer, the term of this patent is extended or adjusted under 35 U.S.C. 154(b) by 811 days.

(21) Appl. No.: 12/239,005

(22) Filed: Sep. 26, 2008

(65) Prior Publication Data
US 2009/0085476 A1    Apr. 2, 2009

(30) Foreign Application Priority Data

Sep. 27, 2007 (KR) .......................... 10-2007-0097301
Oct. 23, 2007 (KR) .......................... 10-2007-0106495

(51) Int. Cl.
| H01L 51/54 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ........ *C07F 15/0033* (2013.01); *H01L 51/0085* (2013.01); *H01L 51/5016* (2013.01); *C09K 11/06* (2013.01); *C09K 2211/1007* (2013.01); *C09K 2211/1029* (2013.01); *C09K 2211/185* (2013.01); *Y10S 428/917* (2013.01)
USPC .......... 428/690; 428/917; 313/504; 313/506; 252/301.16; 257/40; 257/102; 257/103; 257/E51.044; 546/4; 546/10

(58) Field of Classification Search
None
See application file for complete search history.

(56) References Cited

U.S. PATENT DOCUMENTS

| 2003/0072964 A1* | 4/2003 | Kwong et al. ................ 428/690 |
| 2006/0204785 A1* | 9/2006 | Kim et al. .................... 428/690 |
| 2007/0104980 A1* | 5/2007 | Kim et al. .................... 428/690 |

FOREIGN PATENT DOCUMENTS

| CN | 1517427 A | 8/2004 |
| KR | 10-2005-0037479 A | 4/2005 |
| KR | 10-2006-0098859 A | 9/2006 |

* cited by examiner

*Primary Examiner* — Michael H Wilson
(74) *Attorney, Agent, or Firm* — Morgan, Lewis & Bockius LLP

(57) ABSTRACT

The invention relates to a red phosphorescent compound represented by the following Formula (1) and an organic electroluminescent (EL) device using the same:

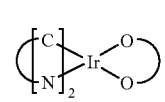

(1)

wherein

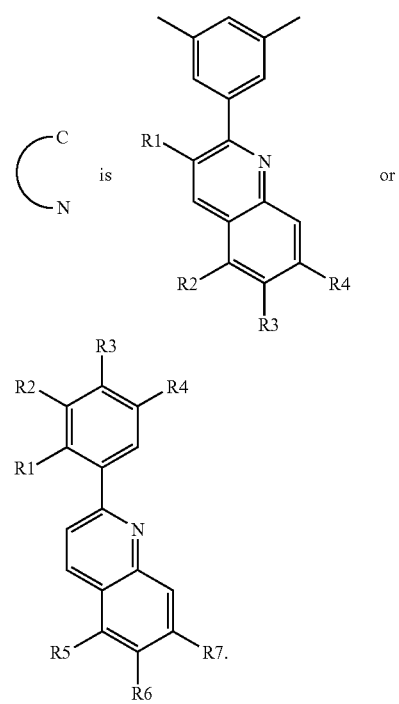

23 Claims, 3 Drawing Sheets

Realate Art

CuPC

NPB

CBP (btp)₂Ir(acac)

BAlq

Alq₃

CuPC

RD1

NPB

RD2

CBP

BAlq

Alq$_3$

RED PHOSPHORESCENT COMPOUND AND ORGANIC ELECTROLUMINESCENT DEVICE USING THE SAME

This application claims the benefits of Korean Patent Application No. 10-2007-097301 filed on Sep. 27, 2007 and of Korean Patent Application No. 10-2007-106495 filed on Oct. 23, 2008, which are hereby incorporated by reference as if fully set forth herein.

BACKGROUND OF THE INVENTION

1. Field of the Invention

The present invention relates to a red phosphorescent compound and an organic electroluminescent device using the same.

2. Discussion of the Related Art

In general, when electric charges are injected into an organic light-emitting layer formed between an electron injecting electrode (cathode) and a hole injecting electrode (anode) of an organic electroluminescent device, electrons combine with holes to create electron-hole pairs, which then decay to emit light.

Organic electroluminescent devices have advantages in that they can be fabricated on flexible transparent substrates (e.g., plastic substrates) and can be operated at a voltage (e.g., 10 V or below) lower than those required to operate plasma display panels (PDPs) and inorganic electroluminescent devices. Other advantages of organic electroluminescent devices are relatively low power consumption and excellent color reproduction.

Further, since organic electroluminescent (EL) devices can emit light of three colors (i.e., green, blue and red), they have been the focus of intense interest lately as next-generation full color display devices.

A general method for fabricating organic EL devices will be briefly explained below.

First, an anode electrode is formed on a transparent substrate.

Indium tin oxide (ITO) is generally used as the anode electrode.

Subsequently, a hole injecting layer (HIL) is formed on the anode electrode. Copper (II) phthalocyanine (CuPc) is mainly used as a material of the hole injecting layer. The hole injecting layer (HIL) is formed to a thickness of about 10 to about 30 nm.

Then, a hole transport layer (HTL) is formed on the hole injecting layer.

The hole transport layer is formed by depositing 4,4'-bis[N-(1-naphthyl)-N-phenylamino]-biphenyl (NPB) to a thickness of about 30 to about 60 nm on the hole injecting layer.

An organic light-emitting layer is formed on the hole transport layer.

If necessary, a dopant may be added to a material for the organic light-emitting layer.

For red phosphorescence emission, 4,4'-N,N'-dicarbazole-biphenyl (CBP) as a material for the organic light-emitting layer is deposited to a thickness of about 30 to about 60 nm on the hole transport layer, and an iridium complex is mainly used as the dopant.

An electron transport layer (ETL) and an electron injecting layer (EIL) are sequentially formed on the organic light-emitting layer. Alternatively, an electron injecting/transport layer is formed on the organic light-emitting layer.

Tris(8-hydroxy-quinolate)aluminum (Alq3) is mainly used as a material of the hole transport layer.

Then, a cathode electrode is formed on the electron injecting layer, and finally a passivation film is formed thereon.

Blue, green and red organic electroluminescent devices can be realized, depending on the formation method of the light-emitting layer.

In the light-emitting layer, holes injected from the anode electrode are recombined with electrons injected from the cathode electrode to form excitons.

The excitons are composed of singlet excitons and triplet excitons present in a ratio of 1:3. Only singlet excitons are used in fluorescence, whereas both singlet excitons and triplet excitons are used in phosphorescence processes to exhibit higher luminescence efficiency.

In particular, the quantum efficiency of red phosphorescent materials is considerably high, compared to that of fluorescent materials. Accordingly, a number of studies associated with the use of red phosphorescent materials in organic electroluminescent devices are being made to enhance the efficiency of the organic electroluminescent devices.

Luminescence efficiency ($\eta_{le}$) is represented by the equation below:

$$\eta_{le} = k \cdot \eta_{int} \cdot \eta_{out}$$

wherein k is human color sensitivity, $\eta_{int}$ is internal quantum efficiency and $\eta_{out}$ is outcoupling efficiency.

In order to obtain high external quantum efficiency, phosphorescent materials for use in organic EL devices must satisfy the requirement of high internal quantum efficiency. However, as shown in FIG. 1, as the color purity of an organic EL device using a red phosphorescent material increases as the x-values on CIE chromaticity coordinates increase), the relative spectral sensitivity of the organic EL device decreases, making it difficult to achieve external quantum efficiency comparable to internal quantum efficiency.

Accordingly, there is a demand for development of a red phosphorescent compound that exhibits high color purity (CIE color purity X≥0.65), high luminescence efficiency, and long luminescence lifetime.

SUMMARY OF THE INVENTION

Accordingly, the present invention is directed to a red phosphorescent compound and an organic electroluminescent (EL) device using the same that substantially obviate one or more problems due to limitations and disadvantages of the related art.

An object of the present invention is to provide a red phosphorescent compound of Formula 1 useful as a dopant of a light-emitting layer, which exhibits high color purity, high luminescence efficiency, and long luminescence lifetime.

Another object of the present invention is to provide an organic electroluminescent (EL) device using the red phosphorescent compound.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a red phosphorescent compound of Formula 1 below:

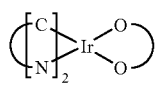

wherein

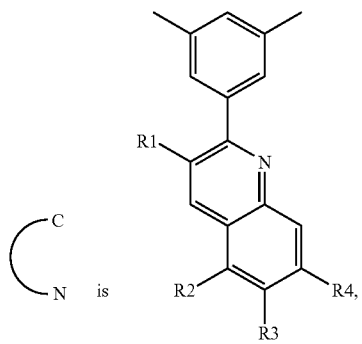

wherein R1, R2, R3 and R4 may be each independently selected from substituted or unsubstituted $C_1$-$C_6$ alkyl, substituted or unsubstituted $C_1$-$C_6$ alkoxy, and combinations thereof, in which at least two of R1, R2, R3 and R4 may be C1-C6 alkyl or C1-C6 alkoxy;

in which the $C_1$-$C_6$ alkyl may be selected from the group consisting of methyl, ethyl, n-propyl, i-propyl, n-butyl, i-butyl and t-butyl, and the $C_1$-$C_6$ alkoxy may be selected from the group consisting of methoxy, ethoxy, n-propoxy, i-propoxy, n-butoxy, i-butoxy and t-butoxy; and R1, R2, R3 and R4 may be each independently selected from a substituted or unsubstituted halogen including F, Cl and Br.

According to the present invention, there is provided an organic electroluminescent (EL) device comprising an anode, a cathode and a light-emitting layer interposed therebetween, wherein the red phosphorescent compound of Formula 1 is used as a dopant for the light-emitting layer.

The light-emitting layer may use, as a host, one selected from an Al complex, a Zn complex and a carbazole derivative.

In Formula 1,

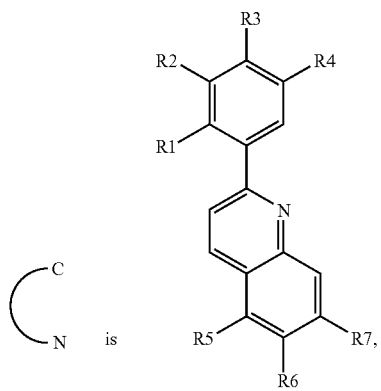

wherein R1, R2, R3 and R4 may be each independently selected from hydrogen, $C_1$-$C_6$ alkyl, and $C_1$-$C_4$ alkoxy, in which at least one of R1, R2, R3 and R4 may be $C_1$-$C_6$ alkyl; and R5, R6 and R7 may be each independently selected from hydrogen, $C_1$-$C_6$ alkyl, $C_1$-$C_4$ alkoxy, and combinations thereof, in which at least two of R5, R6 and R7 may be C1-C6 alkyl or C1-C6 alkoxy, in which the $C_1$-$C_6$ alkyl may be selected from the group consisting of methyl, ethyl, n-propyl, i-propyl, n-butyl, i-butyl and t-butyl, and the $C_1$-$C_4$ alkoxy may be selected from the group consisting of methoxy, ethoxy, n-propoxy, i-propoxy, n-butoxy, i-butoxy and t-butoxy.

According to the present invention, there is provided an organic electroluminescent (EL) device comprising an anode electrode, a cathode electrode and a light-emitting layer interposed therebetween, wherein the red phosphorescent compound of Formula 1 is used as a dopant for the light-emitting layer.

The light-emitting layer may use, as a host, one selected from an Al complex, a Zn complex and a carbazole derivative.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Figure 1:
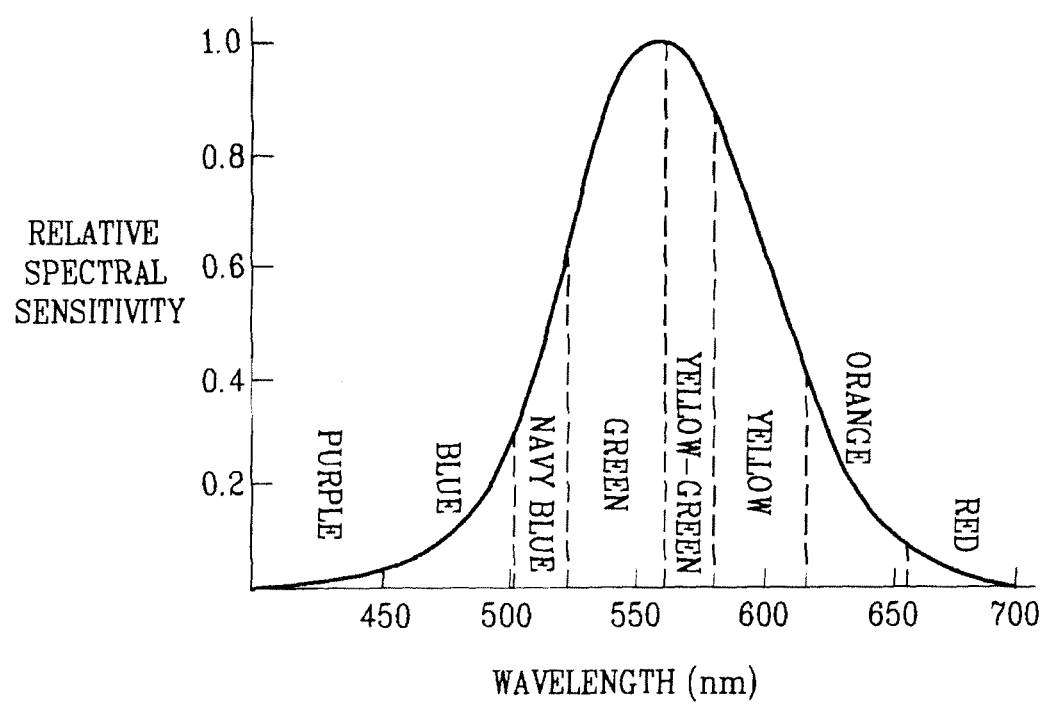
FIG. 1 shows a graph showing a phenomenon wherein, as the color purity of an organic EL device increases, the relative spectral sensitivity of the organic EL device decreases.

The preferred embodiments of the present invention will be illustrated in detail with reference to the annexed drawings.

First Embodiment

A first embodiment of the present invention provides a red phosphorescent compound represented by Formula 1 below:

(1)

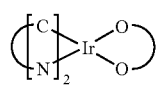

wherein

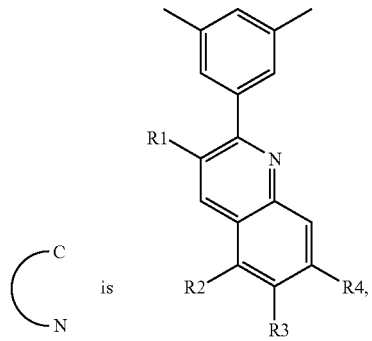

wherein R1, R2, R3 and R4 may be each independently selected from substituted or unsubstituted $C_1$-$C_6$ alkyl, substituted or unsubstituted $C_1$-$C_6$ alkoxy, and combinations thereof, in which at least two of R1, R2, R3 and R4 may be C1-C6 alkyl or C1-C6 alkoxy;

in which the $C_1$-$C_6$ alkyl may be selected from the group consisting of methyl, ethyl, n-propyl, i-propyl, n-butyl, i-butyl and t-butyl, and the $C_1$-$C_6$ alkoxy may be selected from the group consisting of methoxy, ethoxy, n-propoxy, i-propoxy, n-butoxy, i-butoxy and t-butoxy; and R1, R2, R3 and R4 may be selected from a substituted or unsubstituted halogen, including F, Cl and Br.

In Formula 1,

is selected from the group consisting of 2,4-pentanedione

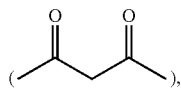

2,2,6,6-tetramethylheptane-3,5-dione

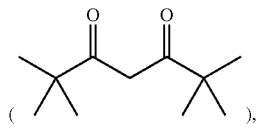

1,3-propanedione

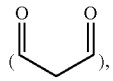

1,3-butanedione

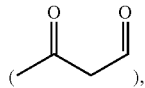

3,5-heptanedione

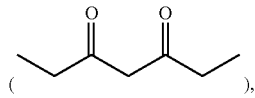

1,1,1-trifluoro-2,4-pentanedione

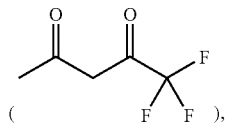

1,1,1,5,5,5-hexafluoro-2,4-pentanedione

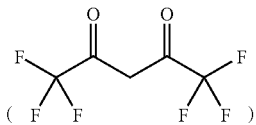 [SMILES: O=C(CC(=O)C(F)(F)F)C(F)(F)F]

and 2,2-dimethyl-3,5-hexanedione

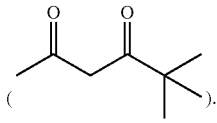

In the first embodiment,

of Formula 1 is selected from the following compounds:

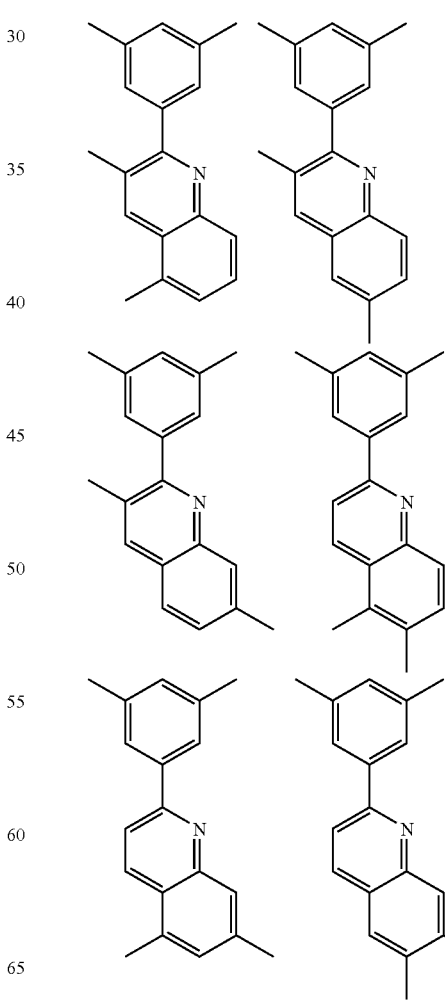

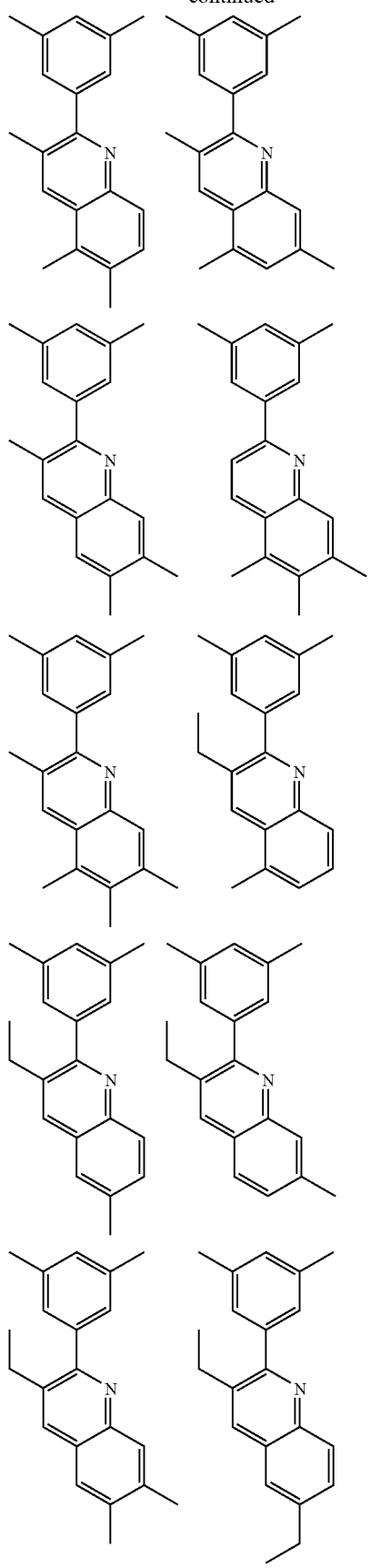
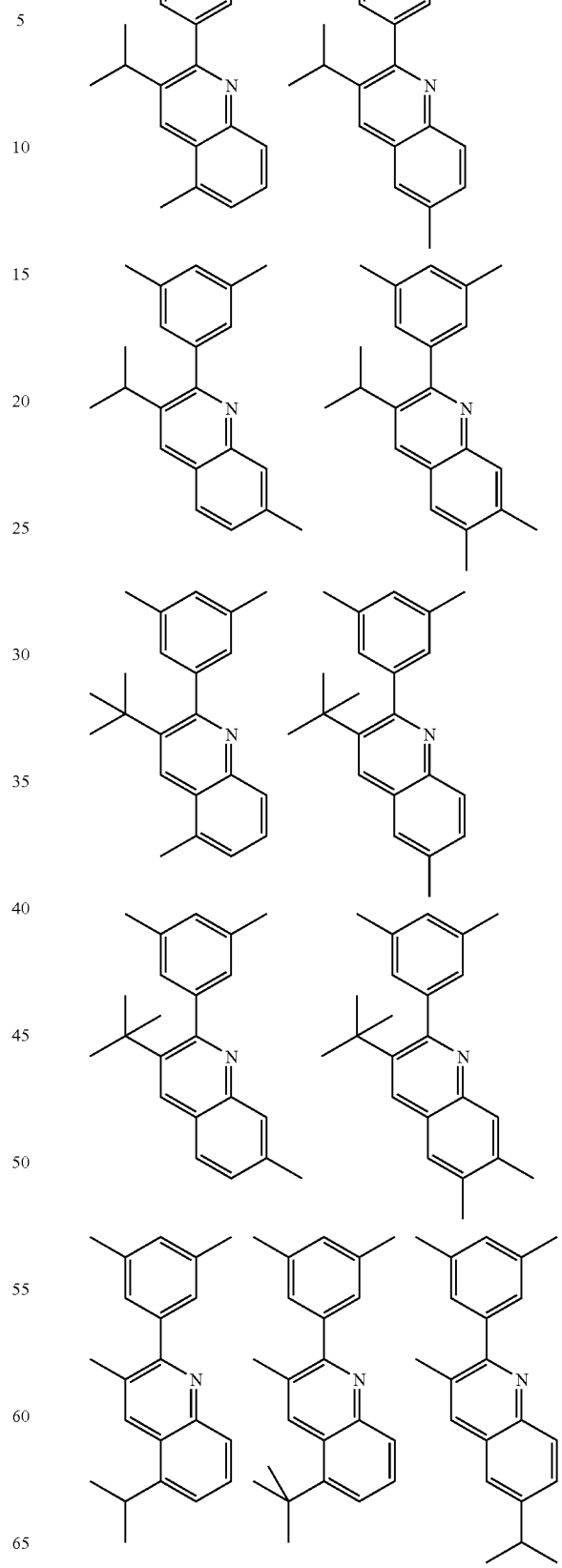

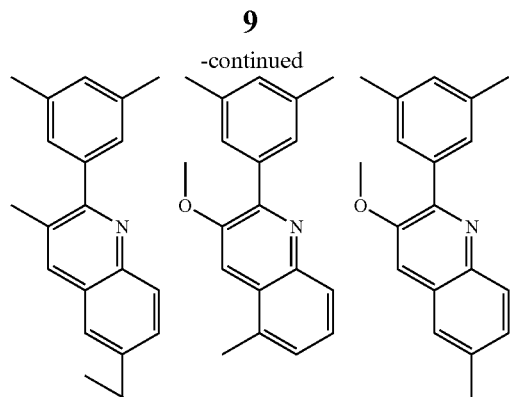
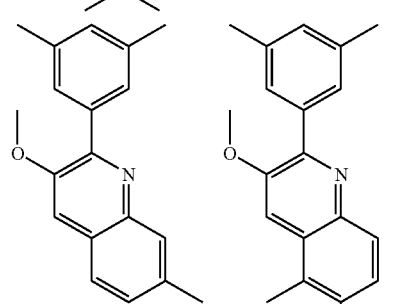
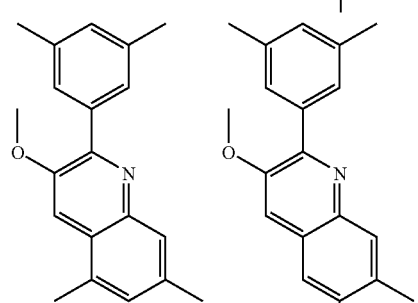
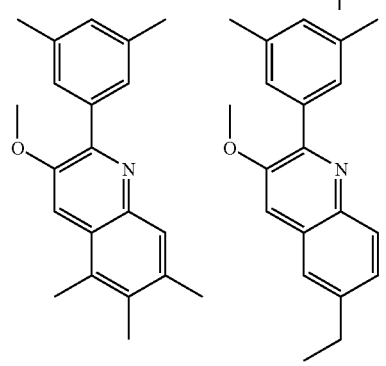
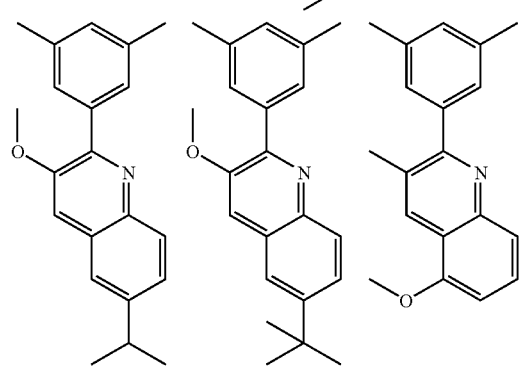
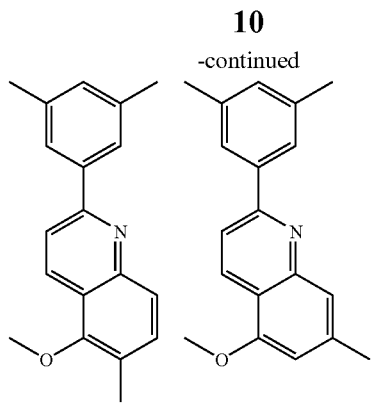
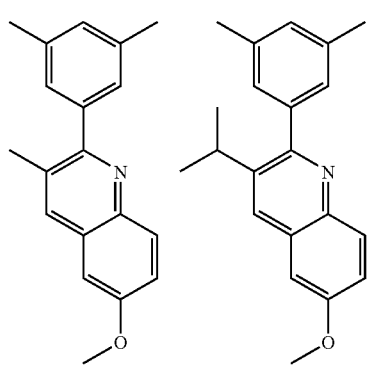
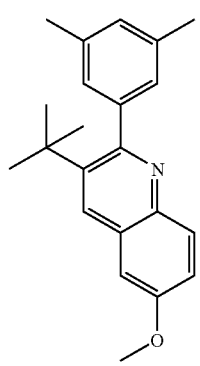
Examples of preferred compounds that can be represented by Formula 1 include the following compounds:
A-1
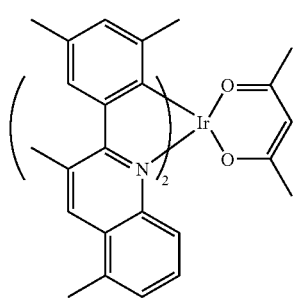

A-2
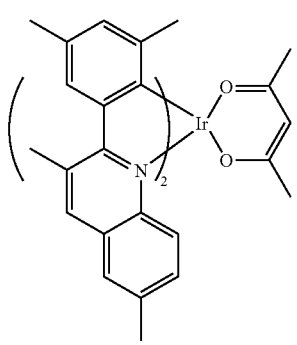
A-3
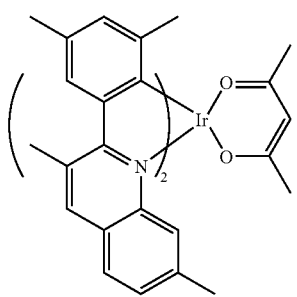
A-4
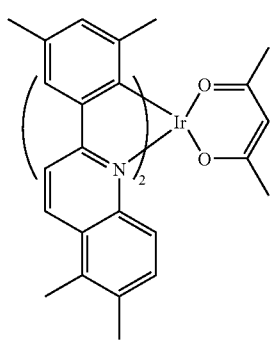
A-5
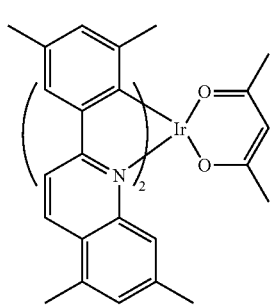
A-6
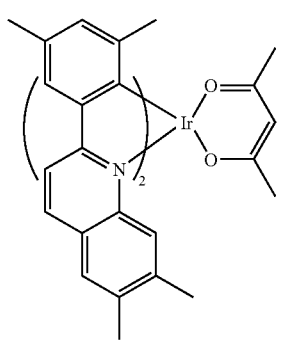
A-7
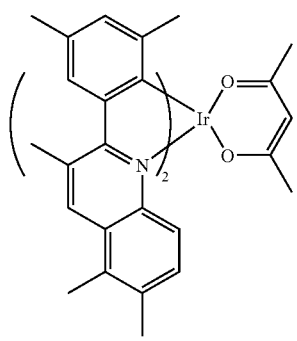
A-8
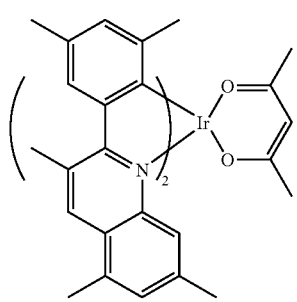
A-9
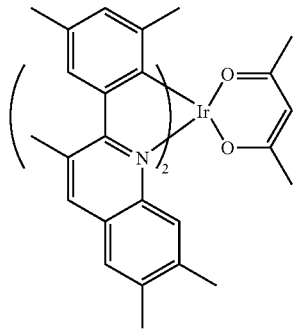
A-10
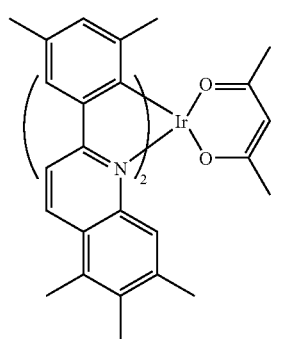
A-11
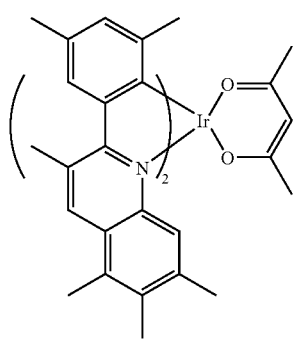

A-12
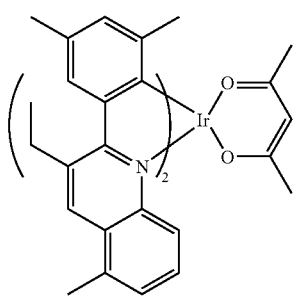
A-13
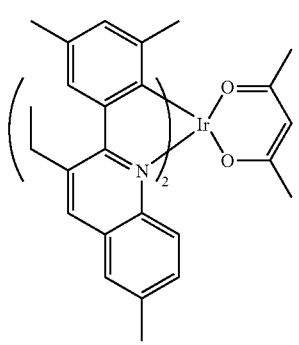
A-14
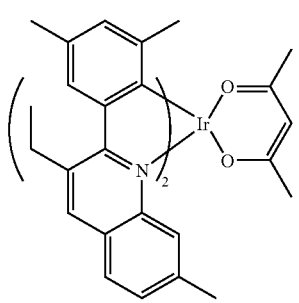
A-15
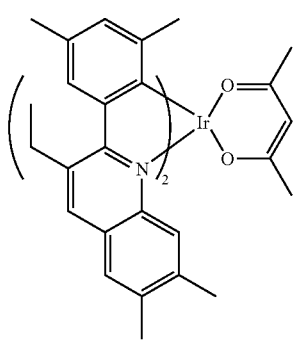
A-16
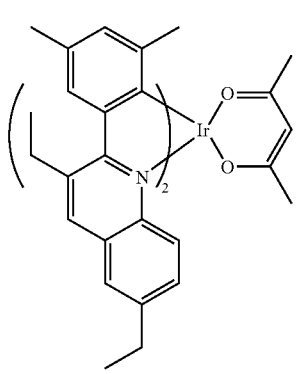
A-17
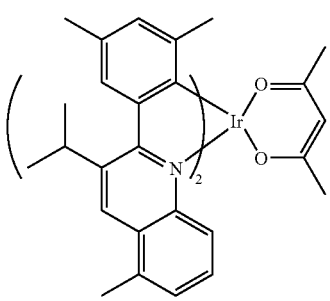
A-18
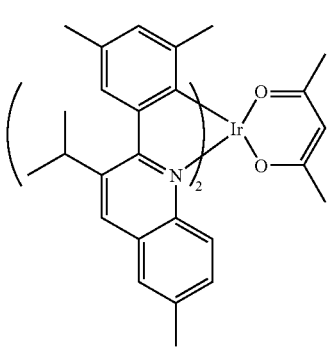
A-19
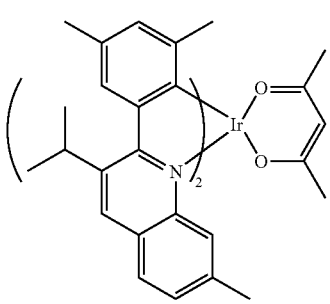
A-20
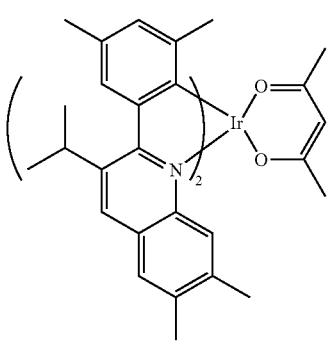
A-21
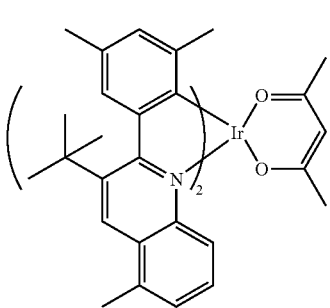

-continued
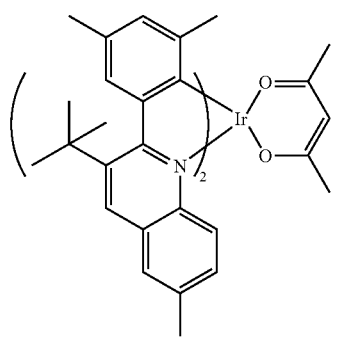
A-22
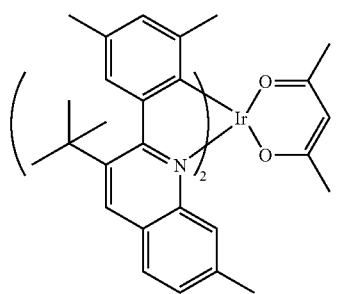
A-23
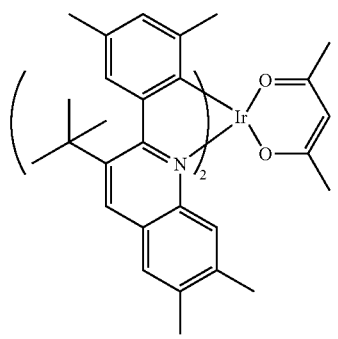
A-24
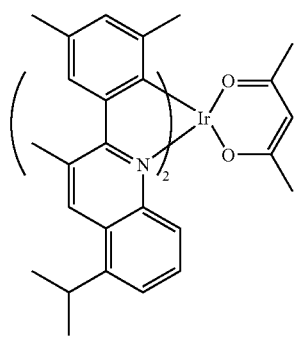
A-25
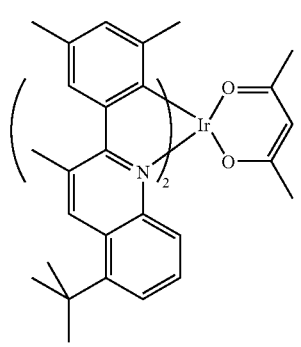
A-26
-continued
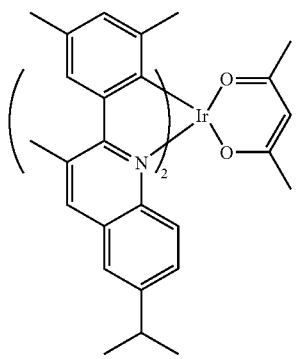
A-27
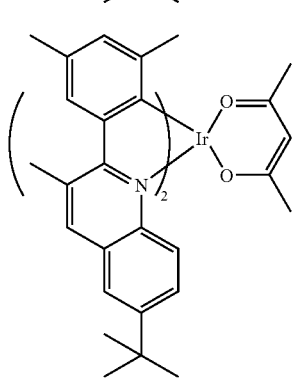
A-28
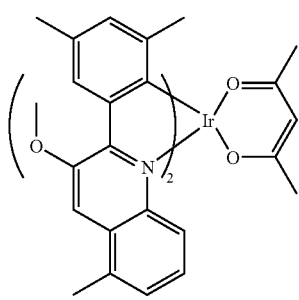
A-29
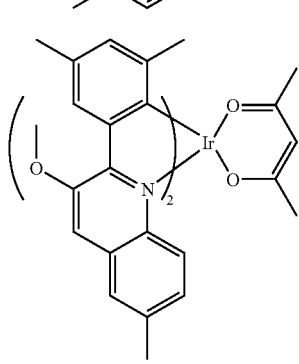
A-30
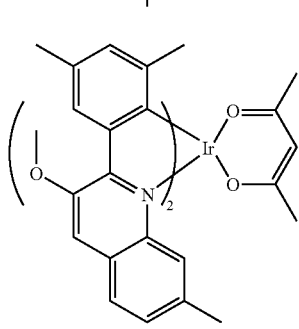
A-31

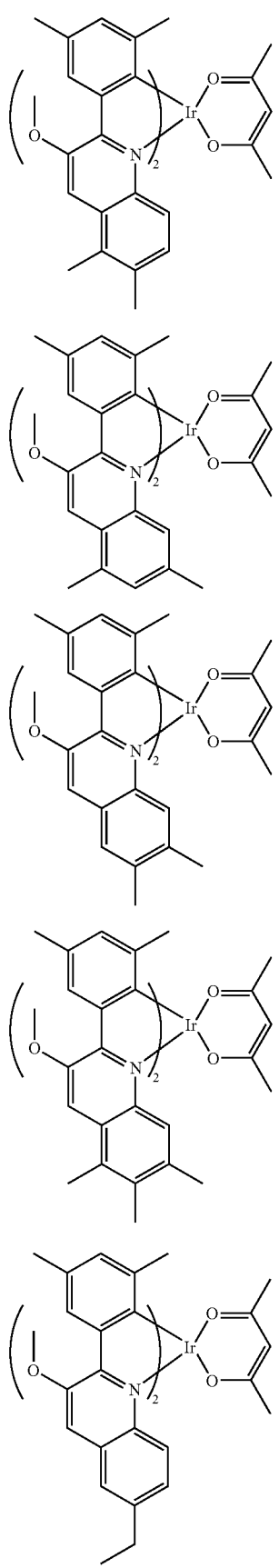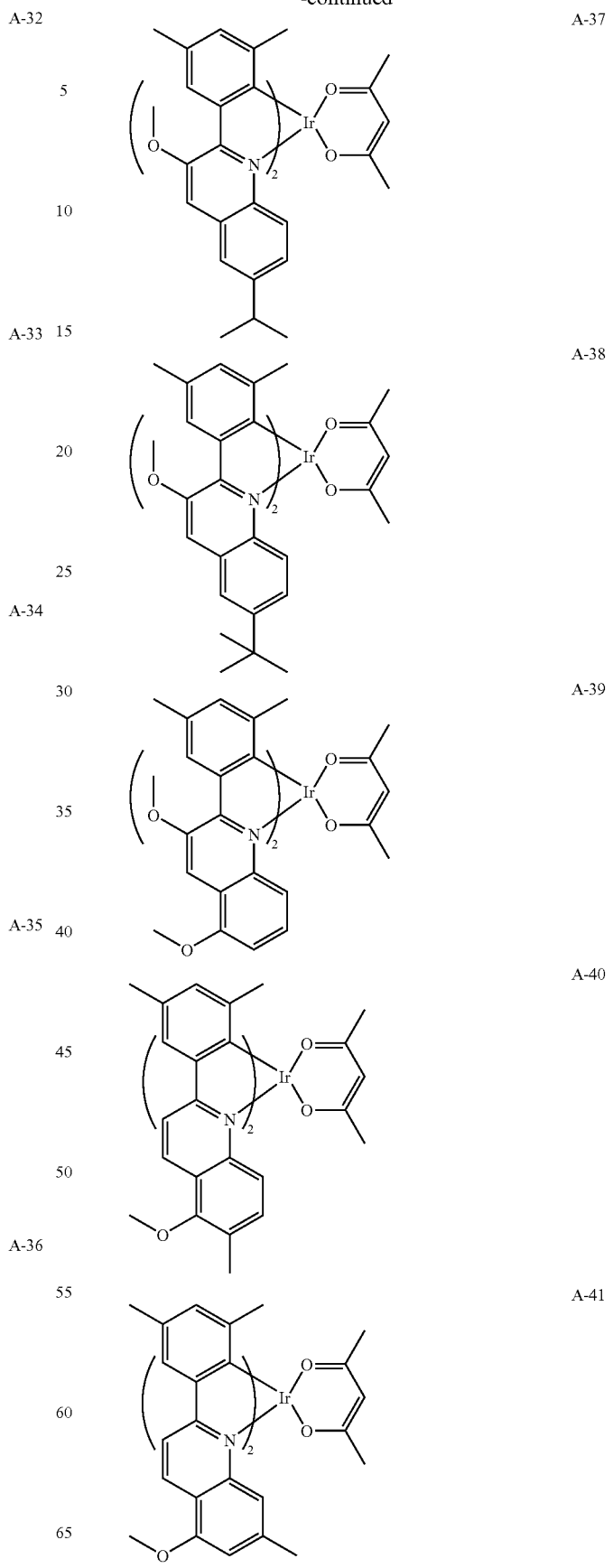

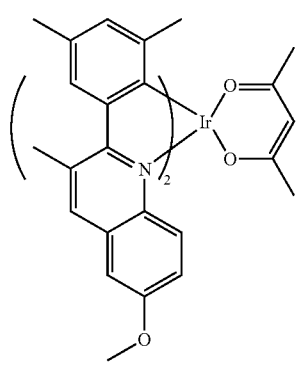
A-42
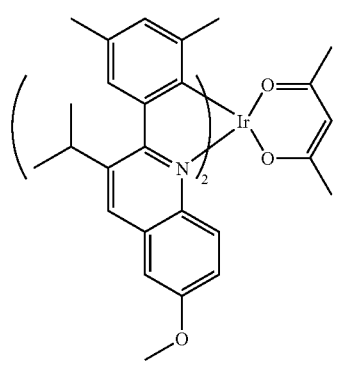
A-43
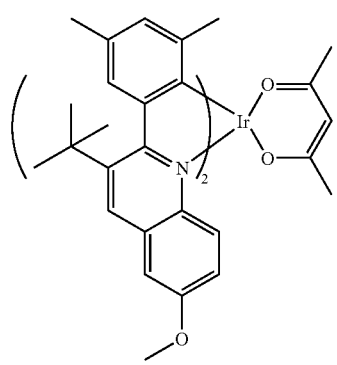
A-44
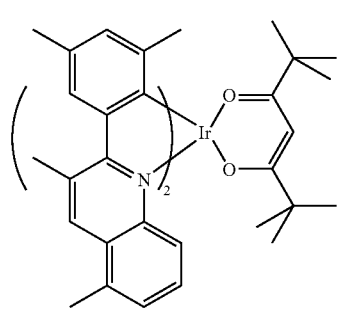
B-1
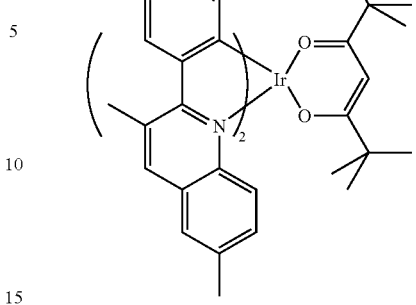
B-2
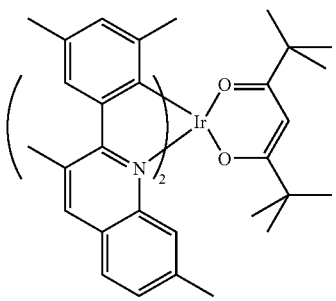
B-3
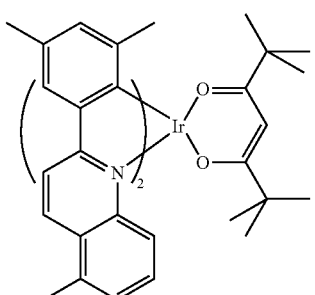
B-4
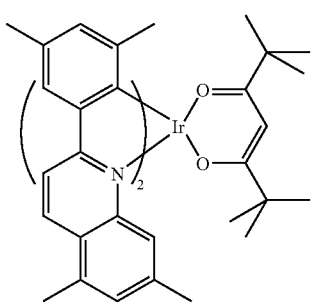
B-5
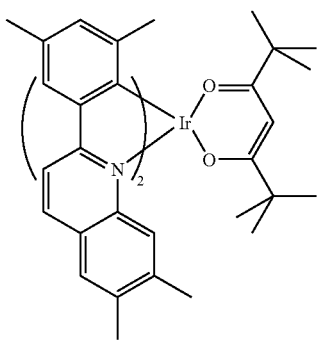
B-6

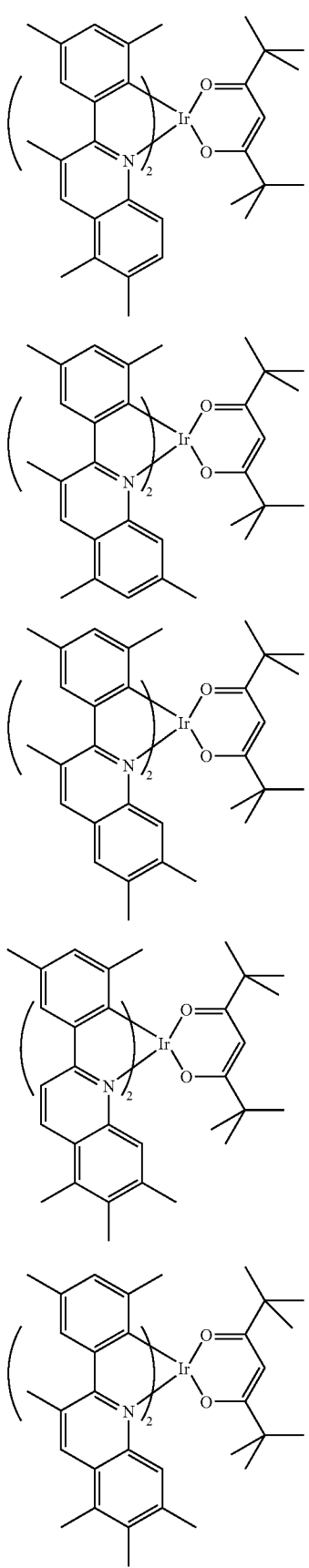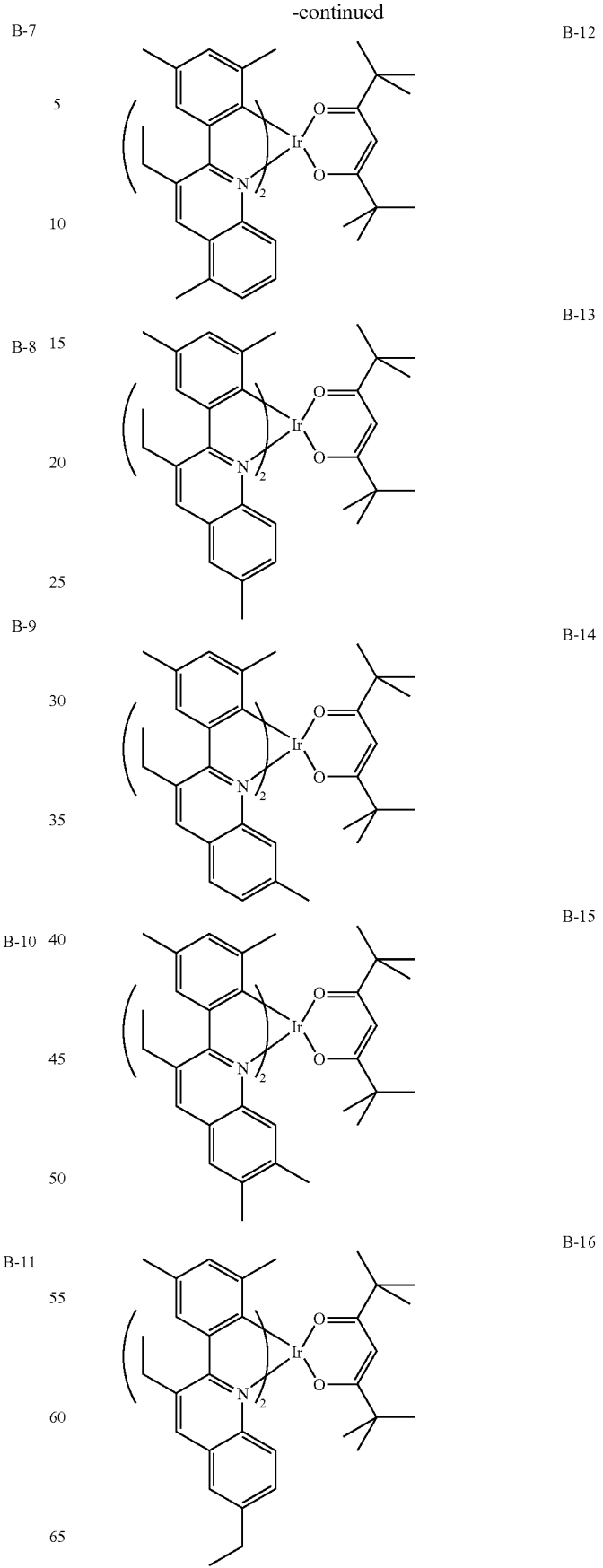

B-17 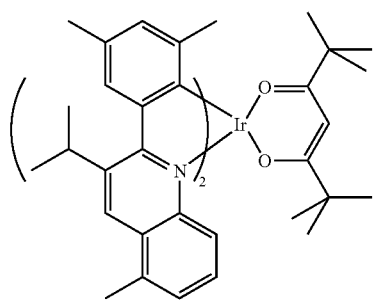
B-18 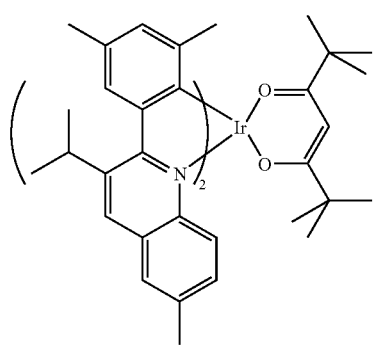
B-19 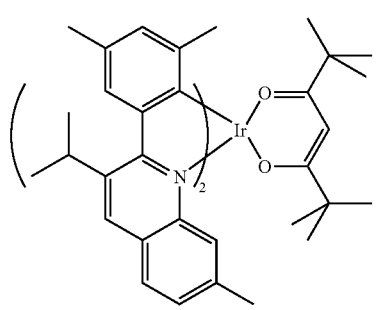
B-20 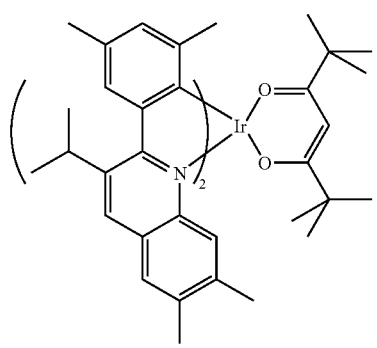
B-21 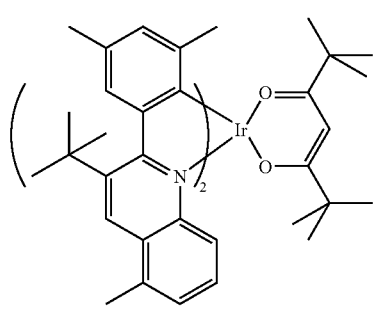
B-22 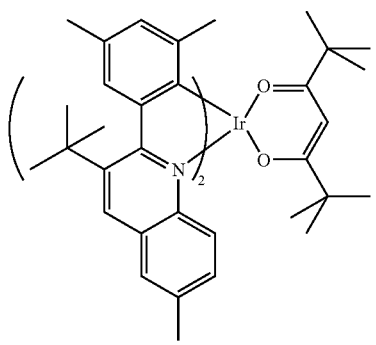
B-23 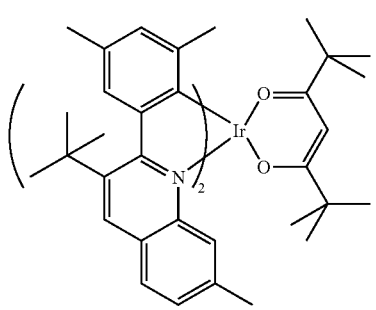
B-24 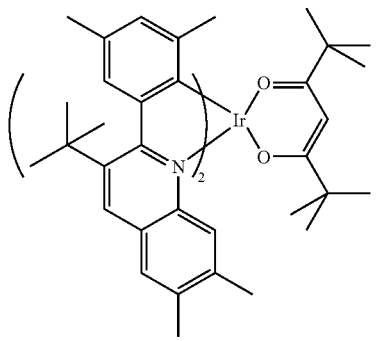
B-25 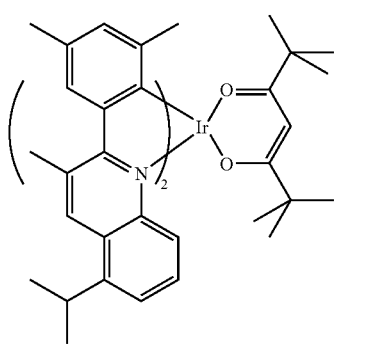

B-26
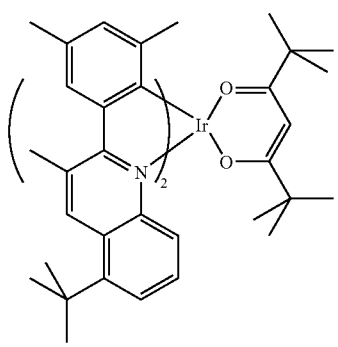
B-27
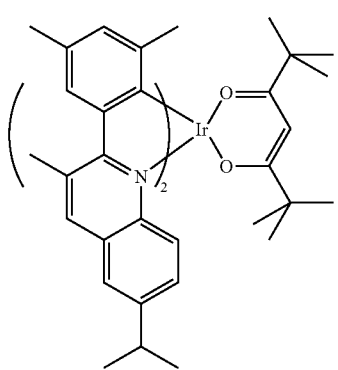
B-28
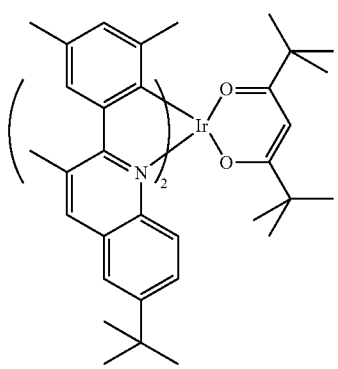
B-29
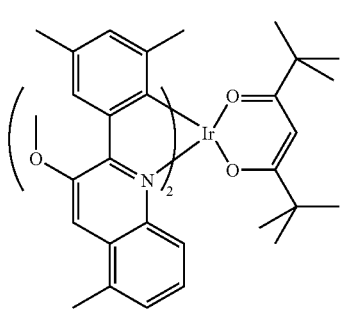
B-30
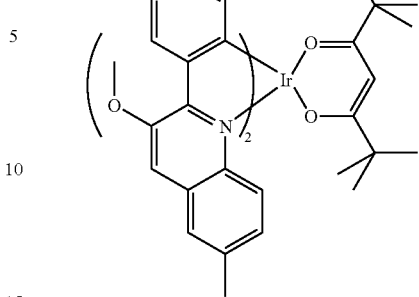
B-31
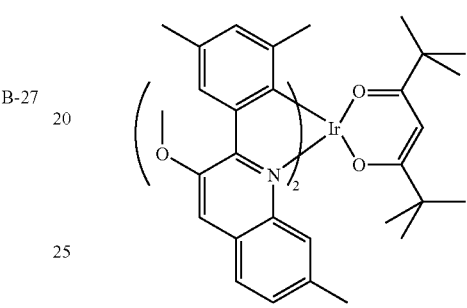
B-32
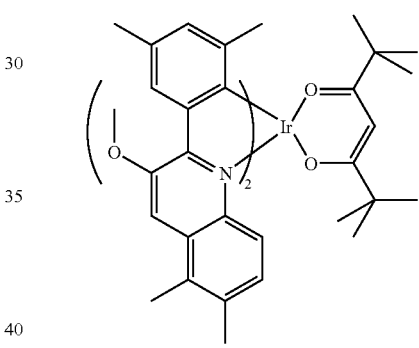
B-33
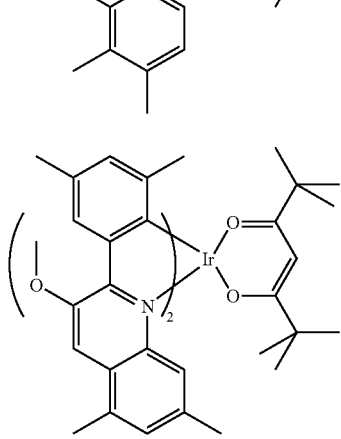
B-34
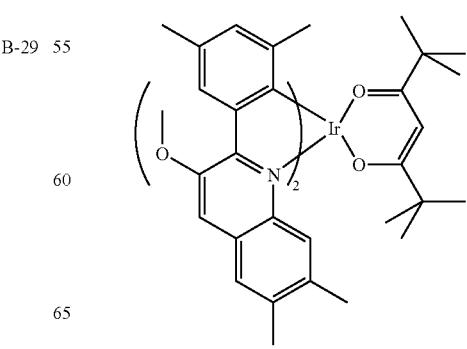

B-35 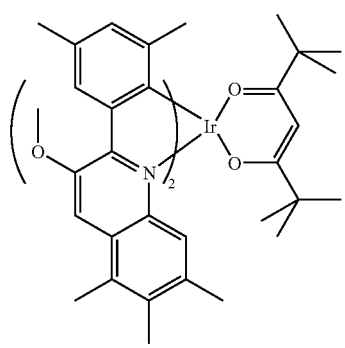
B-36 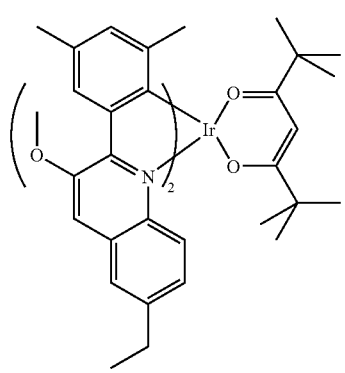
B-37 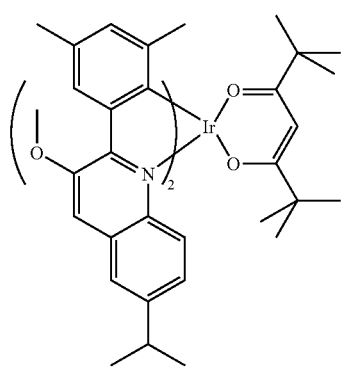
B-38 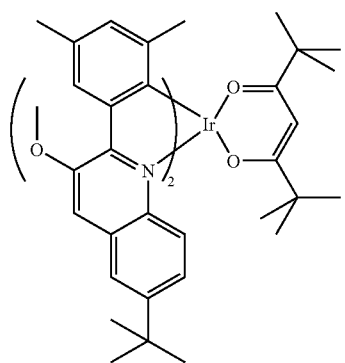
B-39 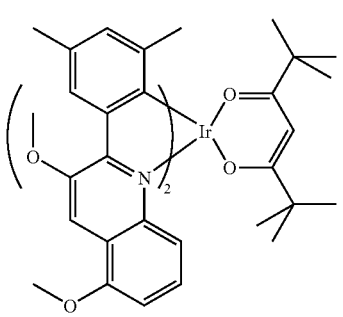
B-40 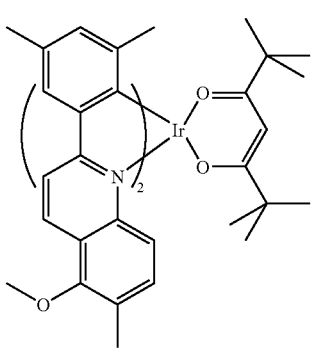
B-41 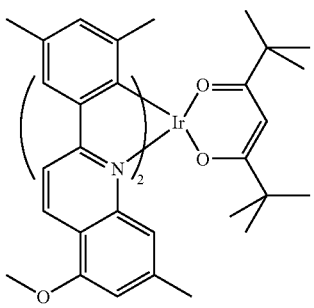
B-42 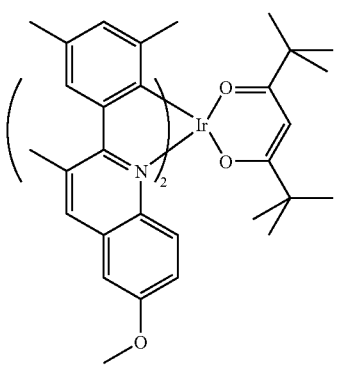

B-43

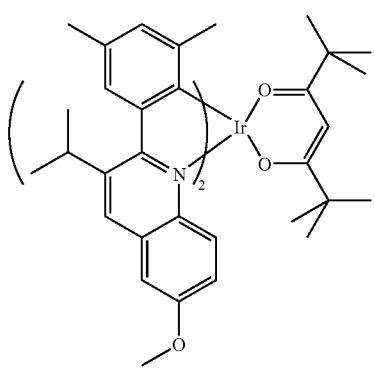

B-44

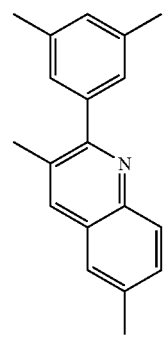

In the first embodiment, the present invention provides an organic electroluminescent (EL) device that has a structure wherein a light-emitting layer is interposed between an anode and a cathode, in which the red phosphorescent compound of Formula 1 is used as a dopant for the light-emitting layer.

The light-emitting layer may use a host selected from Al complexes, Zn complexes and carbazole derivatives.

Preferably, the Al and Zn complexes may have at least one ligand selected from quinol, biphenyl, isoquinol, phenyl, methylquinol, dimethylquinol and dimethylisoquinol, and the carbazole derivative may be 4,4'-N,N' dicarbazole biphenyl (CBP).

Preferably, the dopant is used in an amount of 0.1 to 50% by weight.

Hereinafter, a method for synthesizing some phosphorescent compounds used for organic electroluminescent devices according to the first embodiment of the present invention will be given below.

Synthesis Example (1) Synthesis of 2-(3,5-dimethylphenyl-3,6-dimethylquinoline

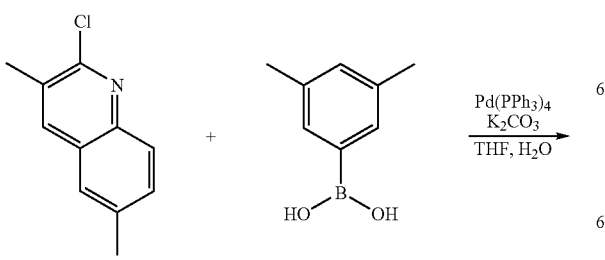

3,5-dimethylphenyl borate (12 mmol), 2-chloro-3,6-dimethylquinoline (10 mmol), tetrakis(triphenylphosphine)palladium(0)(0.5 mmol) and potassium carbonate (30 mmol) are dissolved in tetrahydrofuran (60 ml) and distilled water (20 ml) in a dried two-neck round bottom flask and then stirred at about 100° C. for about 6 hours. After completion of the reaction, the tetrahydrofuran is removed.

Subsequently, the reaction mixture is extracted with dichloromethane and water, distilled under reduced pressure and purified by silica gel column chromatography.

Then, the solvents are distilled under reduced pressure and recrystallized with dichloromethane and petroleum ether. The resulting solid is filtered to yield the target compound, 2-(3,5-dimethylphenyl)-3,6-dimethylquinoline.

(2) Synthesis of Chloro-Crosslinked Dimer Complex

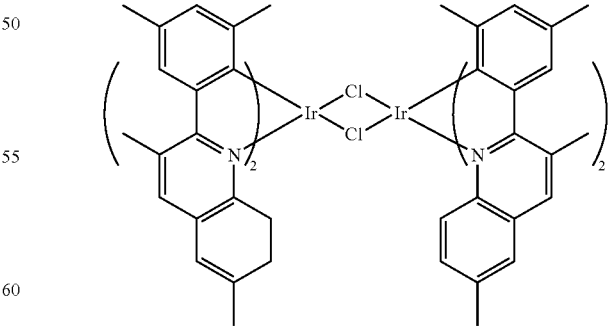

Iridium (III) chloride (5 mmol) and 2-(3,5-dimethylphenyl)-3,6-dimethylquinoline (12 mmol) are added to a mixed solvent (3:1) of 2-ethoxyethanol and distilled water, and then refluxed for about 24 hours.

Then, water is added thereto and the resulting solid is filtered, followed by washing with methanol and petroleum ether to yield the chloro-crosslinked dimer complex.

(3) Synthesis of iridium (III) bis(2-(3,5-dimethylphenyl)-3,6-dimethylquinolinato-N,C$^{2'}$) (2,4-pentanedionate-O,O)

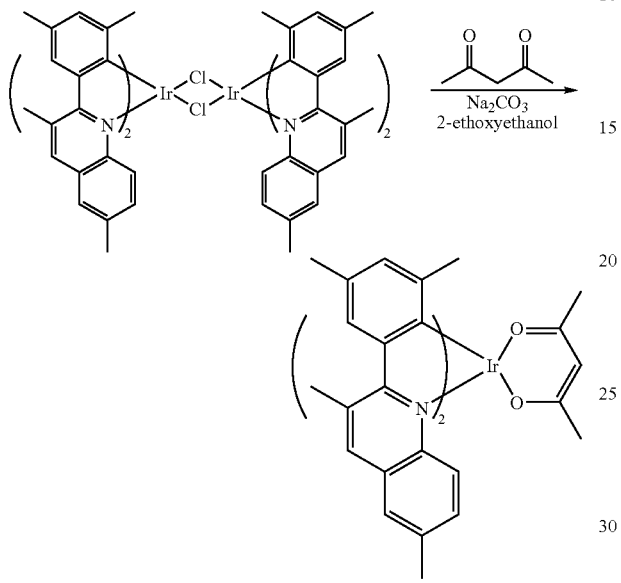

The chloro-crosslinked dimer complex (2 mmol), 2,4-pentanedione (6 mmol) and sodium carbonate (Na$_2$CO$_3$, 6 mmol) are added to 2-ethoxyethanol (30 mL) and then refluxed for about 8 hours.

Then, the reaction mixture is allowed to cool to room temperature and then filtered with addition of distilled water to obtain a solid.

The solid is dissolved in dichloromethane. The solution is filtered through silica gel. The dichloromethane is distilled off under reduced pressure and the residue is washed with methanol and petroleum ether to yield the target compound.

Hereinafter, a detailed description will be made of preferred examples associated with the organic electroluminescent (EL) device according to the present invention.

Figure 2:
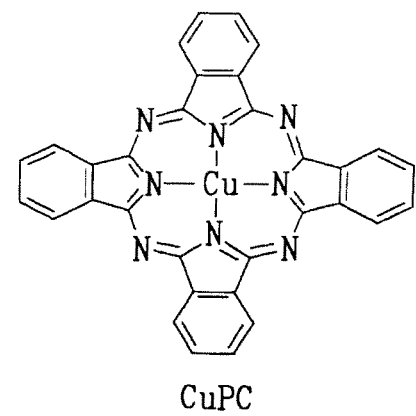
FIG. 2 shows structural formulas of organic compounds used in the first embodiment of the present invention.
Figure 2:
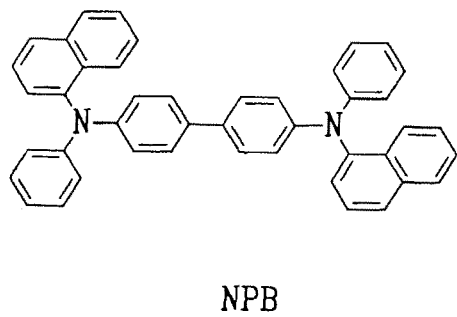
Figure 2:
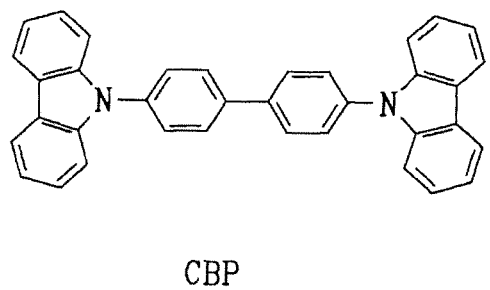
Figure 2:
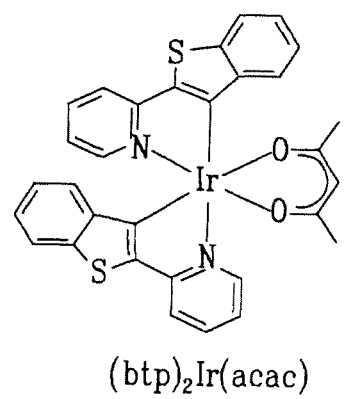
Figure 2:
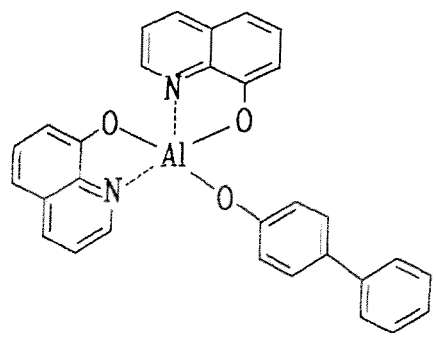
Figure 2:
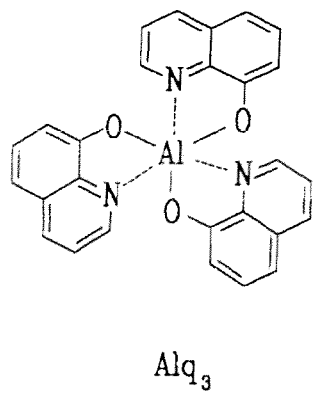

FIG. 2 shows structural formulas of organic compounds used in the first embodiment of the present invention.

EXAMPLES

Example 1

An ITO glass substrate was patterned such that it had a light-emitting area of 3 mm×3 mm, followed by cleaning. After the patterned substrate was disposed in a vacuum chamber, the base pressure of the chamber was adjusted to 1×10$^{-6}$ torr.

Then, the organic compounds shown in FIG. 2, i.e., CuPc (200 Å), NPB (400 Å), BAlq+A-2 (7%) (200 Å), Alq3 (300 Å), LiF (5 Å) and Al (1,000 Å) were sequentially deposited on the ITO glass substrate to fabricate an organic EL device.

The organic EL device thus fabricated exhibited a luminance of 926 cd/m$^2$ and a voltage of 6.0 V at an electric current of about 0.9 mA. At this time, the CIE chromaticity coordinates were x=5.681 and y=0.311.

The lifetime (defined as the time taken before the luminance of the organic EL device decreases to half its initial value) of the organic EL device was 4,300 hours at about 2,000 cd/m$^2$.

Example 2

An ITO glass substrate was patterned such that it had a light-emitting area of 3 mm×3 mm, followed by cleaning.

After the patterned substrate was disposed in a vacuum chamber, the base pressure of the chamber was adjusted to 1×10$^{-6}$ torr.

Then, the organic compounds shown in FIG. 2, i.e., CuPc (200 Å), NPB (400 Å), BAlq+A-27 (7%) (200 Å), Alq3 (300 Å), LiF (5 Å) and Al (1,000 Å) were sequentially deposited on the ITO glass substrate to fabricate an organic EL device.

The organic EL device thus fabricated exhibited a luminance of 838 cd/m$^2$ and a voltage of 5.8 V at an electric current of about 0.9 mA. At this time, the CIE chromaticity coordinates were x=0.683 and y=0.307.

The lifetime (defined as the time taken before the luminance of the organic EL device decreases to half its initial value) of the organic EL device was about 4,100 hours at about 2,000 cd/m$^2$.

Example 3

An ITO-coated glass substrate was patterned such that it had a light-emitting area of 3 mm×3 mm, followed by cleaning.

After the patterned substrate was disposed in a vacuum chamber, the base pressure of the chamber was adjusted to 1×10$^{-6}$ torr.

Then, the organic compounds shown in FIG. 2, i.e., CuPc (200 Å), NPB (400 Å), BAlq+B-3 (7%) (200 Å), Alq3 (300 Å), LiF (5 Å) and Al (1,000 Å) were sequentially deposited on the ITO glass substrate to fabricate an organic EL device.

The organic EL device thus fabricated exhibited a luminance of 1,020 cd/m$^2$ and a voltage of 5.8 V at an electric current of about 0.9 mA. At this time, the CIE chromaticity coordinates were x=0.680 and y=0.312.

The lifetime (defined as the time taken before the luminance of the organic EL device decreases to half its initial value) of the organic EL device was about 3,800 hours at about 2,000 cd/m$^2$.

Comparative Example

An ITO glass substrate was patterned such that it had a light-emitting area of 3 mm×3 mm, followed by cleaning.

Subsequently, the patterned substrate was disposed in a vacuum chamber and the base pressure of the chamber was adjusted to 1×10$^{-6}$ torr.

Then, the organic compounds shown in FIG. 2, i.e., CuPc (200 Å), NPB (400 Å), (btp)2Ir(acac)(7%)(200 Å), Alq3 (300 Å), LiF (5 Å) and Al (1,000 Å), were sequentially deposited on the ITO glass substrate to fabricate an organic EL device.

The organic EL device thus fabricated exhibited a luminance of 790 cd/m$^2$ and a voltage of 7.5 V at an electric current of about 0.9 mA. At this time, the CIE chromaticity coordinates were x=0.659 and y=0.329.

The lifetime (defined as the time taken before the luminance of the organic EL device decreases to half its initial value) of the organic EL device was about 2,500 hours at about 2,000 cd/m$^2$.

The organic EL devices fabricated in the Examples and Comparative Example were evaluated for efficiency, CIE chromaticity coordinates, luminance and lifetime properties. The results are shown in Table 1.

TABLE 1

| Device | Voltage (V) | Electric current (mA) | Luminance (cd/m²) | Current efficiency (cd/A) | Power efficiency (lm/W) | CIE (X) | CIE (Y) | Life time (h) (half the initial luminance) |
|---|---|---|---|---|---|---|---|---|
| Ex. 1 | 6.0 | 0.9 | 926 | 9.26 | 4.85 | 0.681 | 0.311 | 4300 |
| Ex. 2 | 5.8 | 0.9 | 838 | 8.38 | 4.54 | 0.683 | 0.307 | 4100 |
| Ex. 3 | 5.8 | 0.9 | 1020 | 10.20 | 5.52 | 0.680 | 0.312 | 3800 |
| Comp. Ex. | 7.5 | 0.9 | 780 | 7.80 | 3.27 | 0.659 | 0.329 | 2500 |

As can be seen from Table 1 above, the organic EL devices of the present invention exhibits an operation voltage of at least about 6.0 V or less, a luminance of at east about 800 cd/m² or higher, and a lifetime of about 3,500 hours or longer.

Second Embodiment

A detailed description of the red phosphorescent compound according to the second embodiment of the present invention will be given below.

In the second embodiment, provided is a red phosphorescent compound that exhibits improved color purity by substituting phenyl with at least one alkyl, and at the same time, exhibits high luminescence efficiency and long luminescence lifetime by substituting nitrogen-free phenyl of the quinoline with at least two of alkyl and alkoxy.

The red phosphorescent compound of the second embodiment is also represented by Formula 1 as above.

However, in the second embodiment,

in Formula 1 is

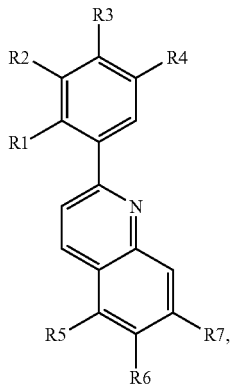

wherein R1, R2, R3 and R4 may be each independently selected from hydrogen, $C_1$-$C_6$ alkyl and $C_1$-$C_4$ alkoxy, in which at least one of R1, R2, R3 and R4 may be $C_1$-$C_6$ alkyl; and R5, R6 and R7 may be each independently selected from hydrogen, $C_1$-$C_6$ alkyl, $C_1$-$C_4$ alkoxy, and combinations thereof, in which at least two of R5, R6 and R7 may be C1-C6 alkyl or C1-C6 alkoxy, in which the $C_1$-$C_6$ alkyl is selected from the group consisting of methyl, ethyl, n-propyl, i-propyl, n-butyl, i-butyl and t-butyl, and the $C_1$-$C_4$ alkoxy is selected from the group consisting of methoxy, ethoxy, n-propoxy, i-propoxy, n-butoxy, i-butoxy and t-butoxy.

In the second embodiment,

of Formula 1 may be one of 2,4-pentanedione

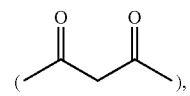

2,2,6,6-tetramethylheptane-3,5-dione

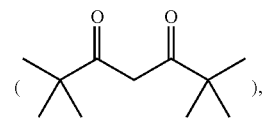

1,3-propanedione

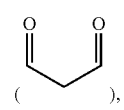

1,3-butanedione

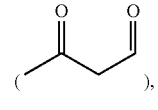

3,5-heptanedione

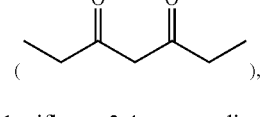

1,1,1-trifluoro-2,4-pentanedione

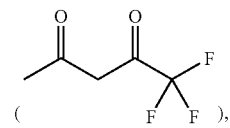

1,1,1,5,5,5-hexafluoro-2,4-pentanedione
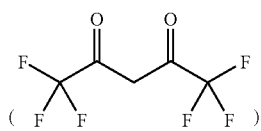 [SMILES: O=C(CC(=O)C(F)(F)F)C(F)(F)F]
and 2,2-dimethyl-3,5-hexanedione
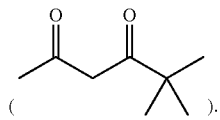
That is,
of the second embodiment is the same as the first embodiment.
In the second embodiment,
of Formula 1 is selected from the following compounds:
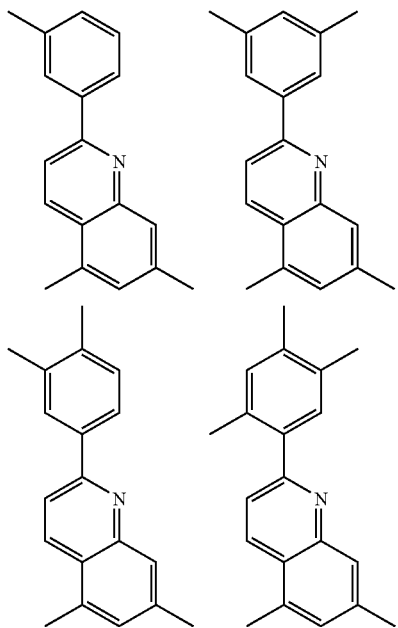
-continued
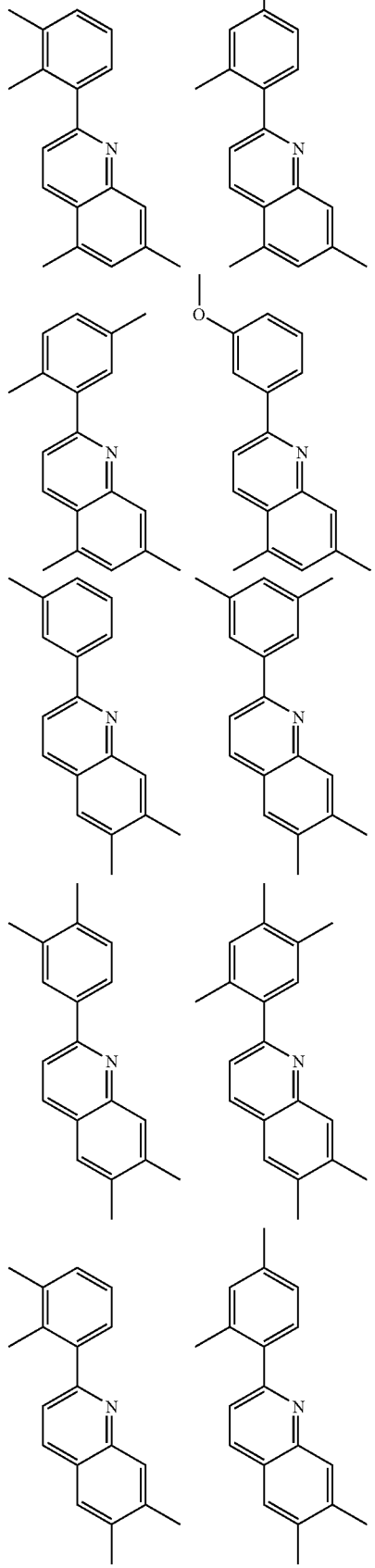

-continued
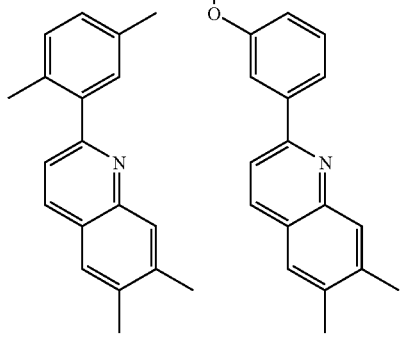 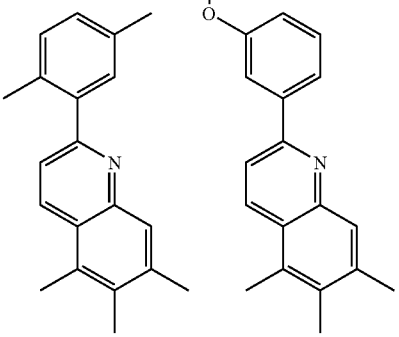
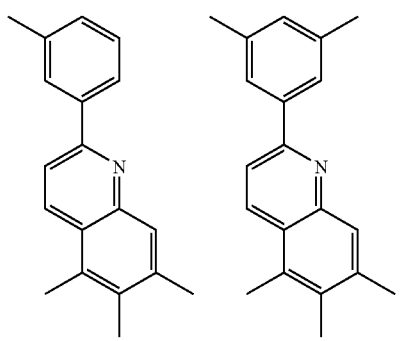 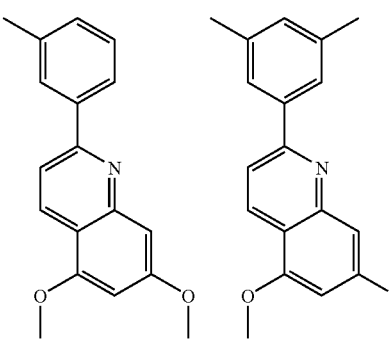
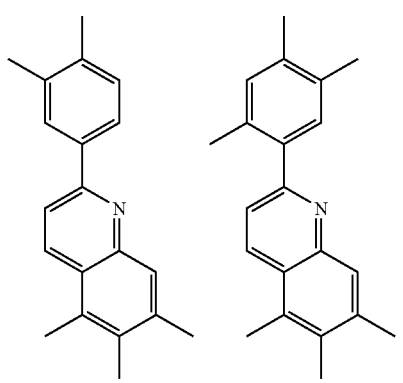 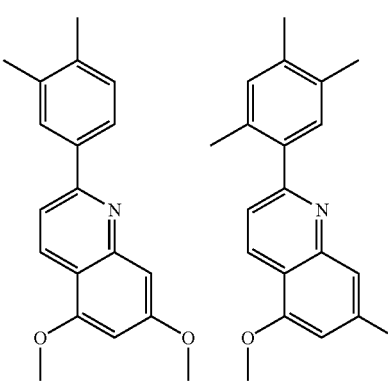
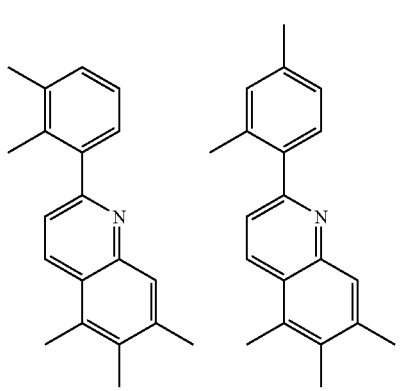 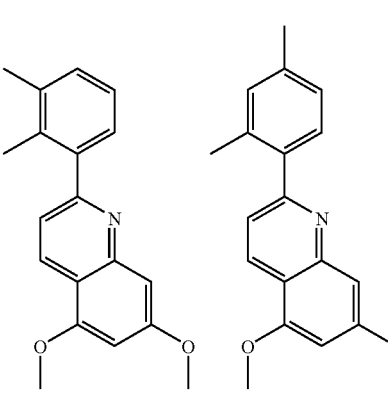

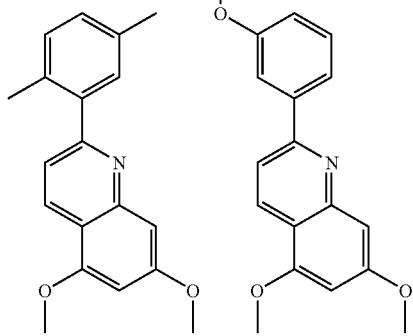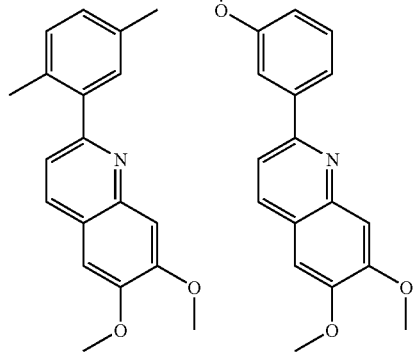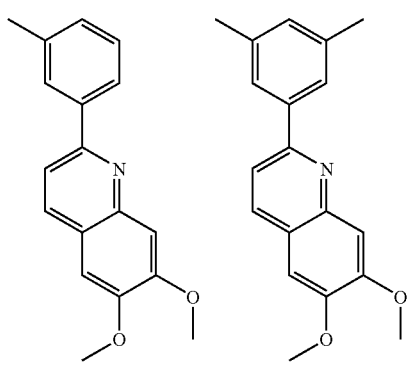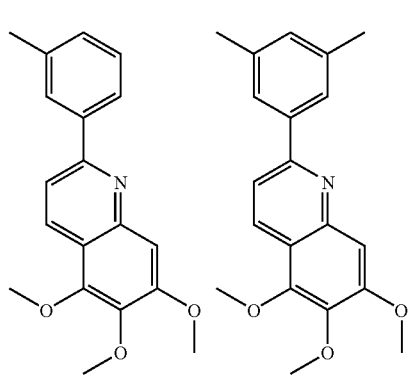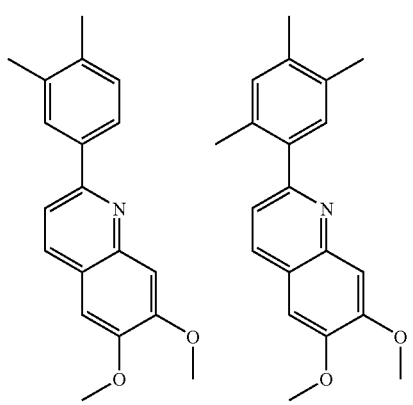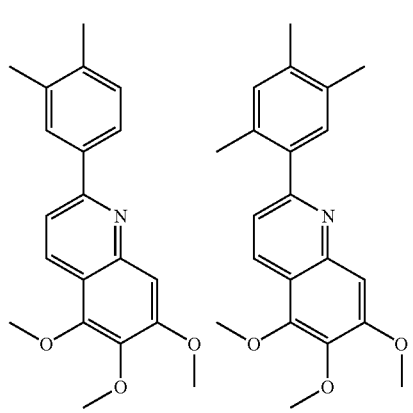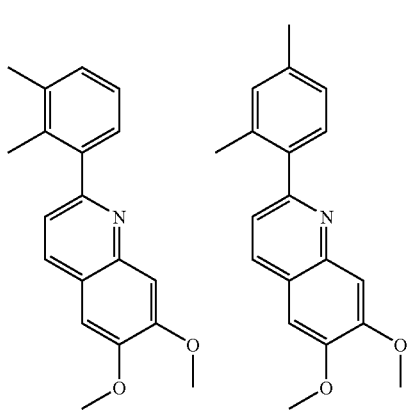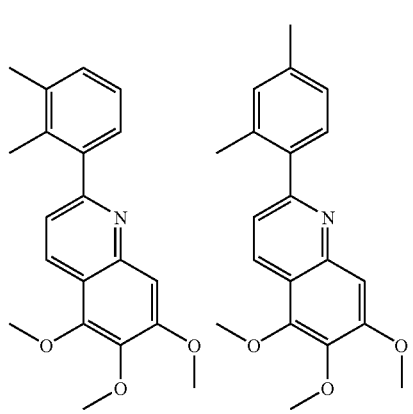

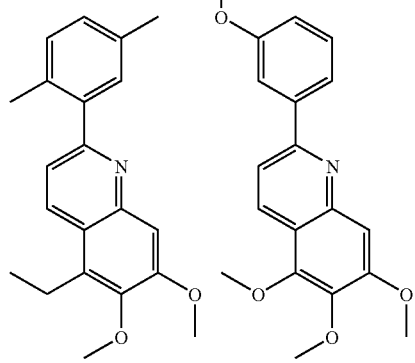 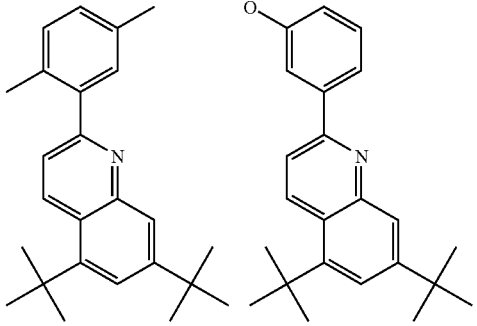
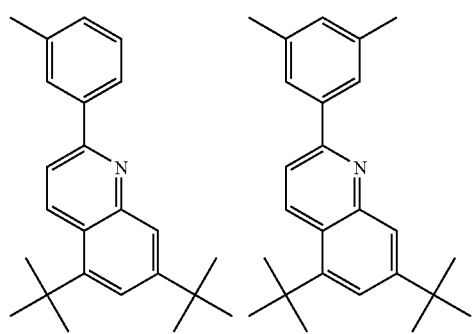 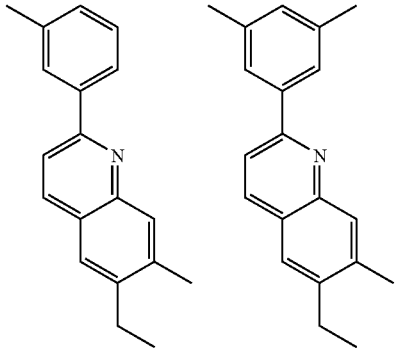
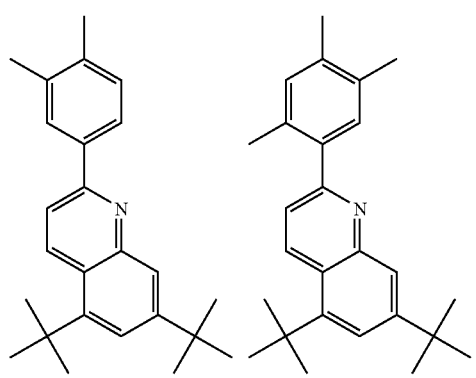 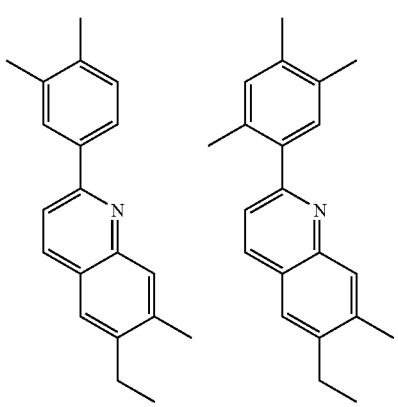
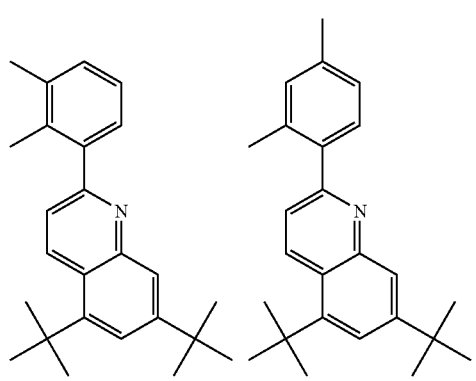 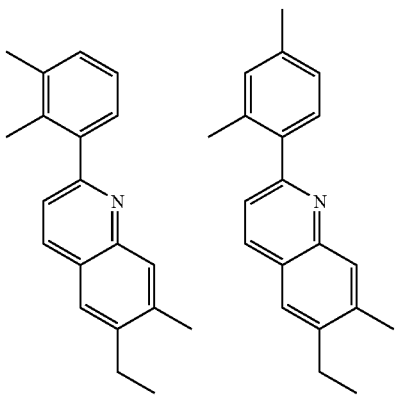

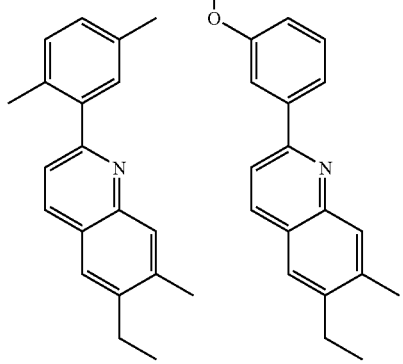
That is, the second embodiment is different from the first embodiment in
of Formula 1.
In the second embodiment, examples of preferred compounds that can be represented by Formula 1 include the following compounds:
A-1
A-2
A-3
A-4
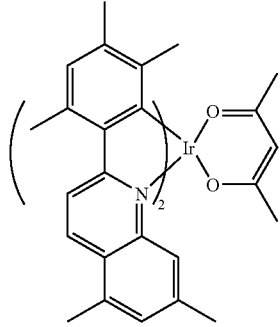
A-5
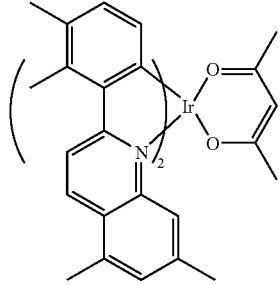
A-6
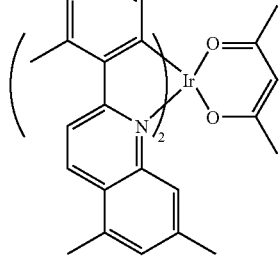
A-7
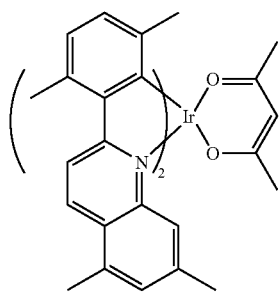
A-8
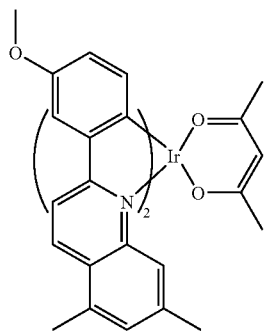

A-9
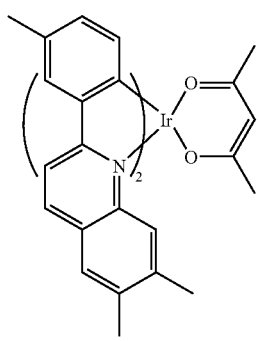
A-10
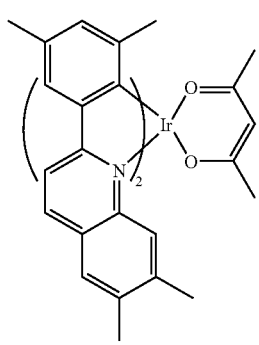
A-11
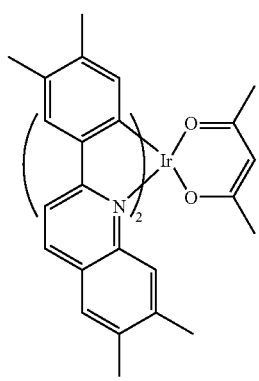
A-12
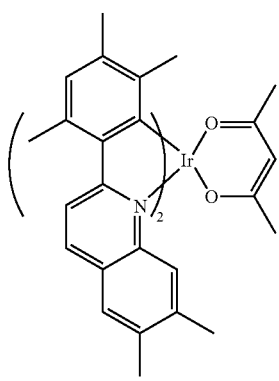
A-13
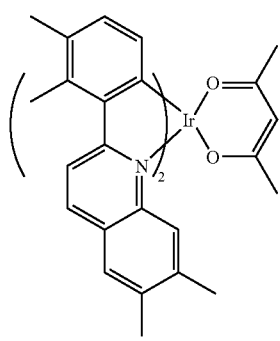
A-14
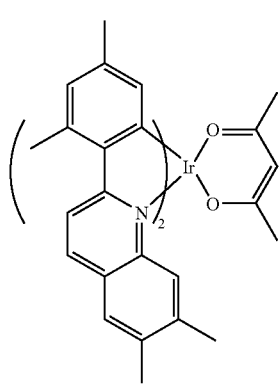
A-15
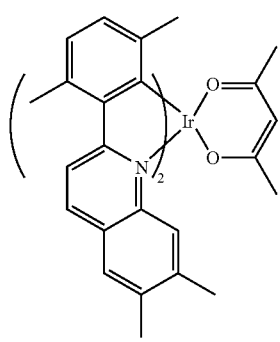
A-16
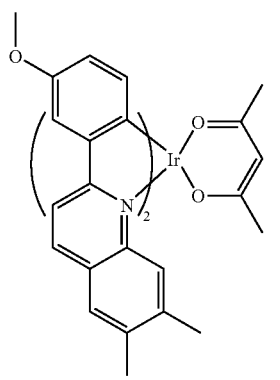

-continued
A-17
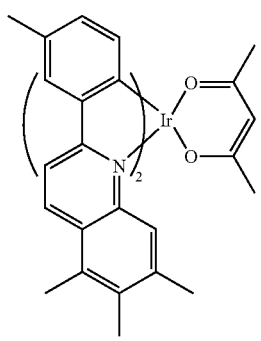
A-18
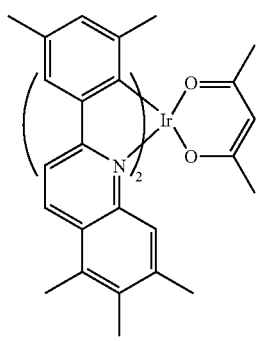
A-19
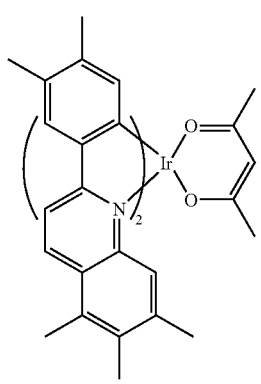
A-20
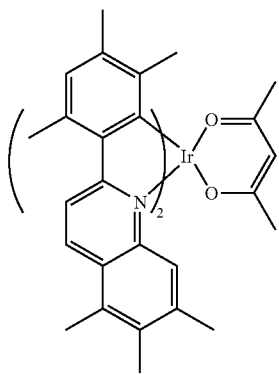
-continued
A-21
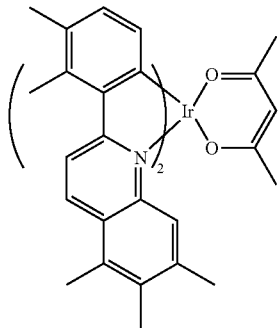
A-22
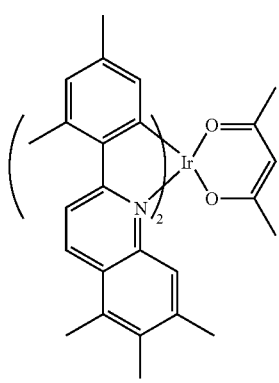
A-23
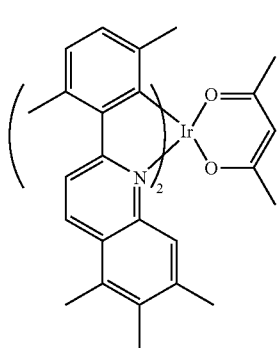
A-24
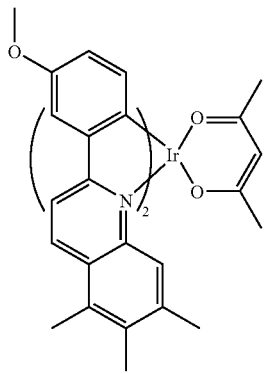

A-25
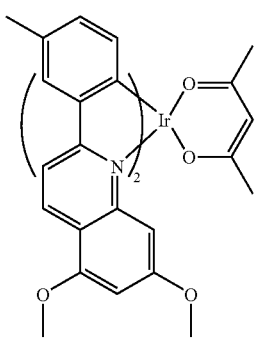
A-26
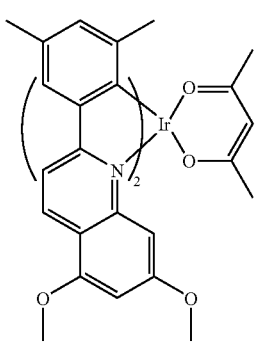
A-27
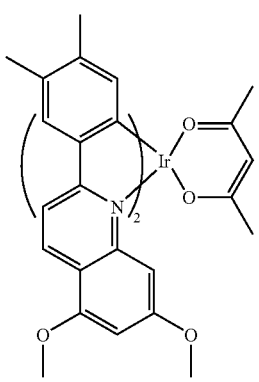
A-28
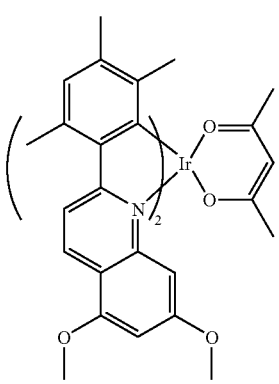
A-29
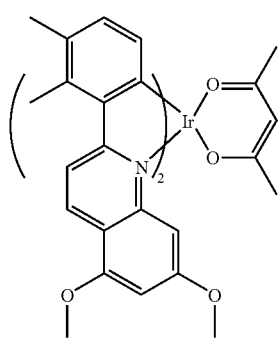
A-30
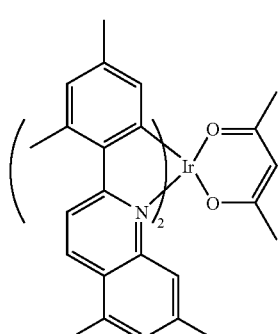
A-31
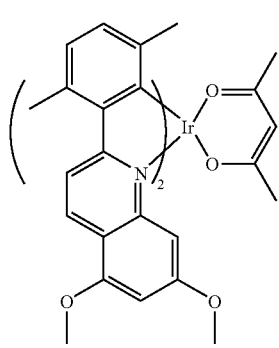
A-32
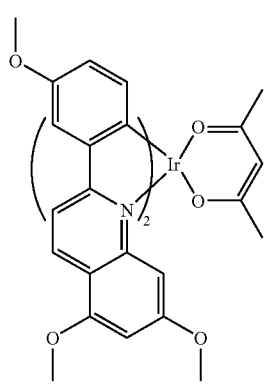

A-33
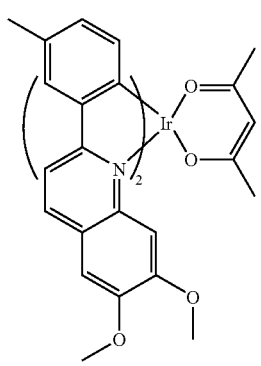
A-34
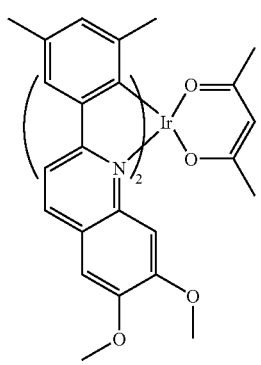
A-35
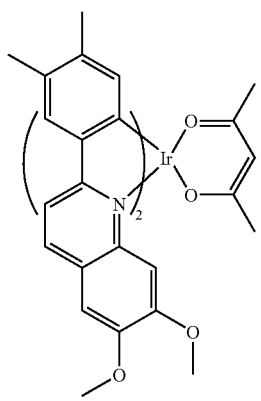
A-36
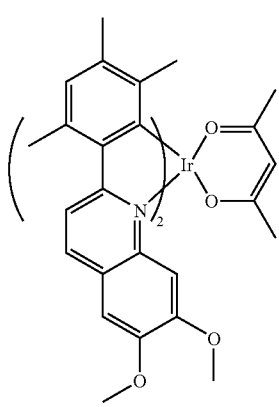
A-37
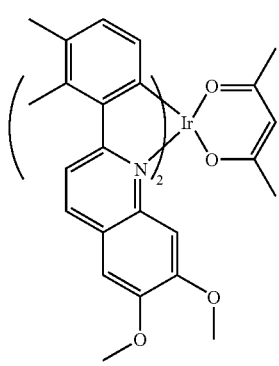
A-38
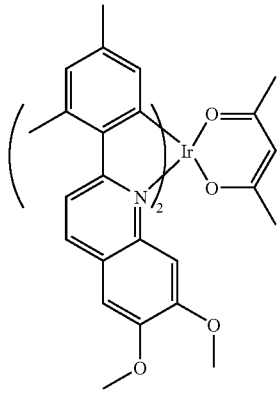
A-39
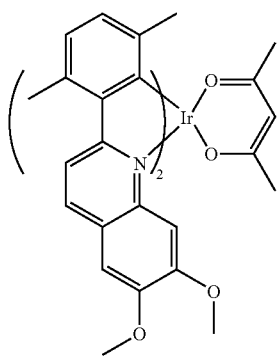
A-40
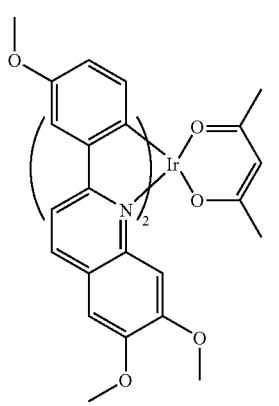

A-41
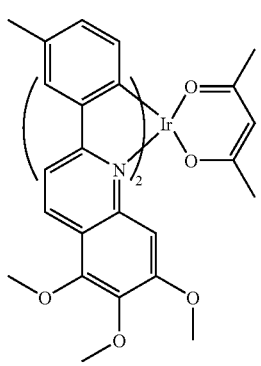
A-42
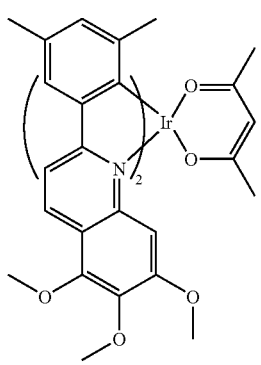
A-43
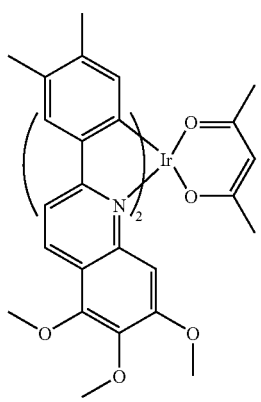
A-44
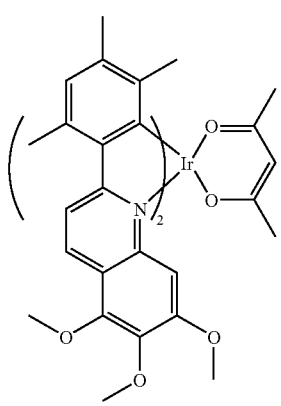
A-45
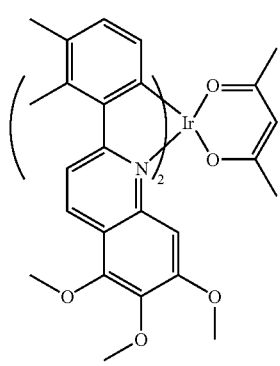
A-46
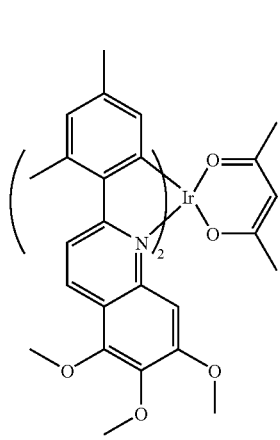
A-47
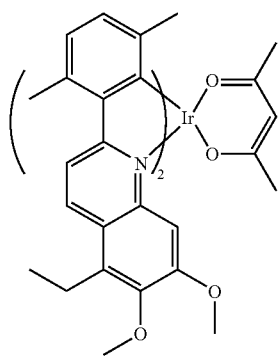
A-48
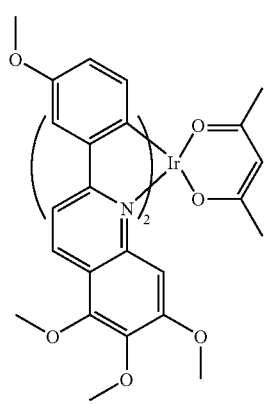

A-49
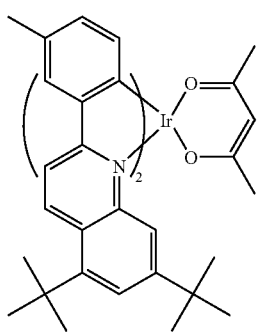
A-50
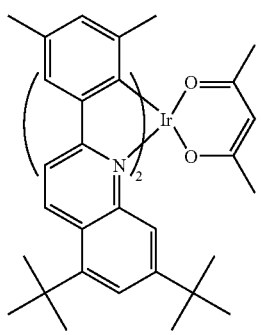
A-51
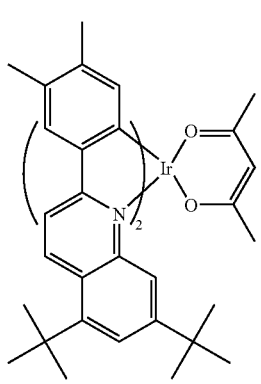
A-52
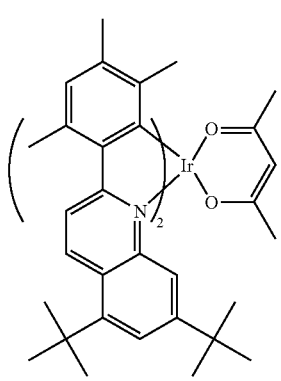
A-53
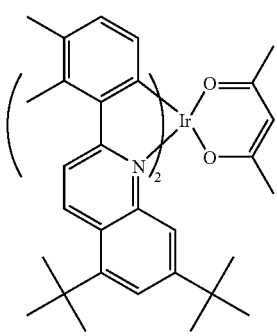
A-54
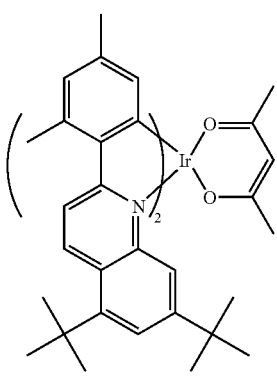
A-55
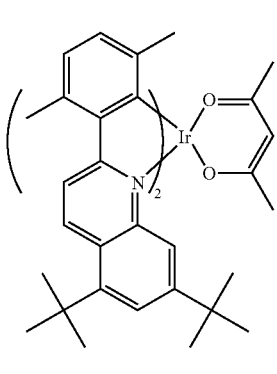
A-56
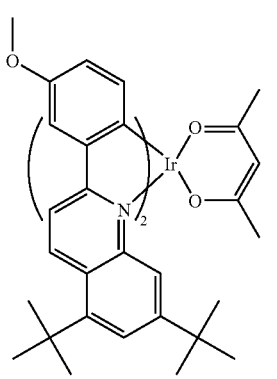

-continued
A-57
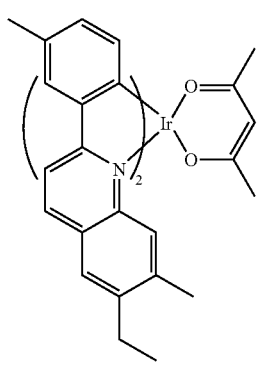
A-58
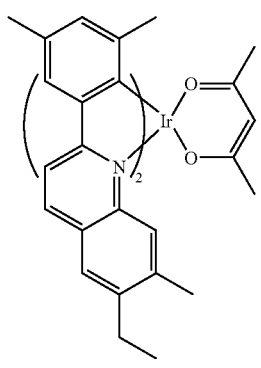
A-59
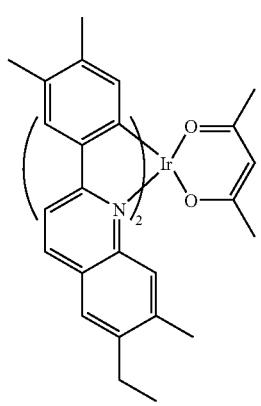
A-60
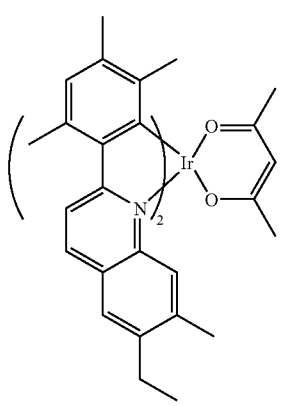
-continued
A-61
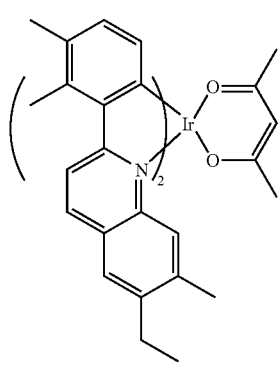
A-62
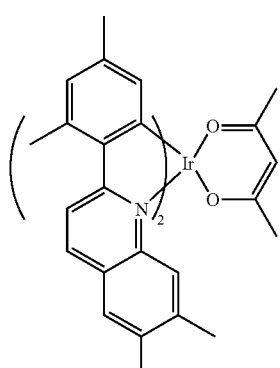
A-63
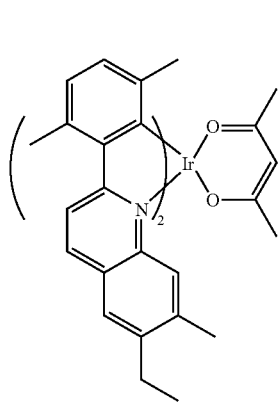
A-64
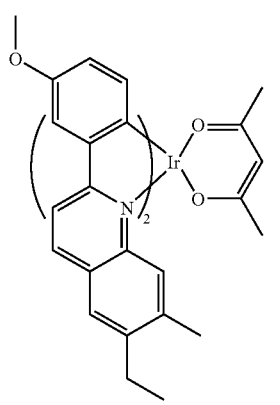

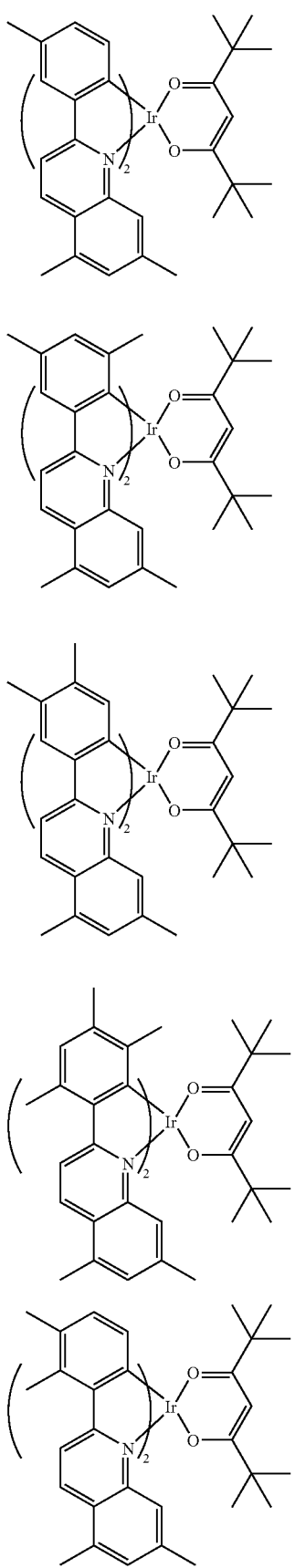
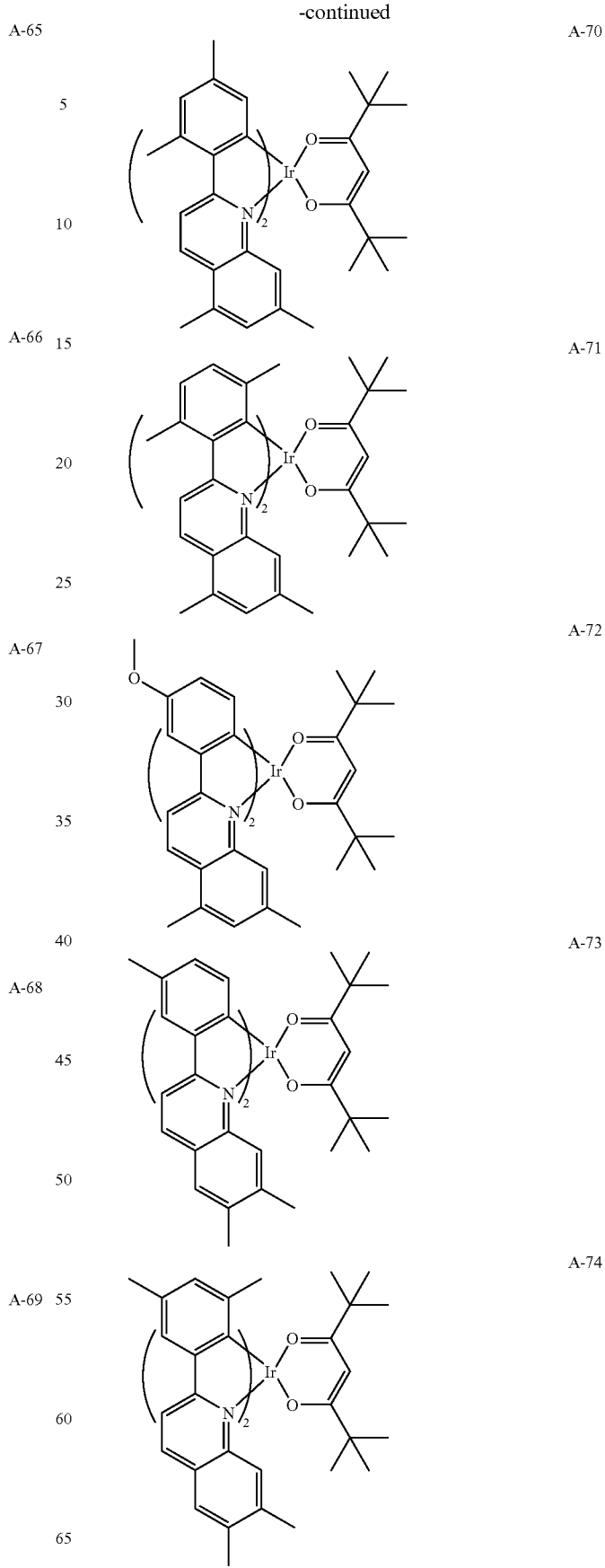

A-75 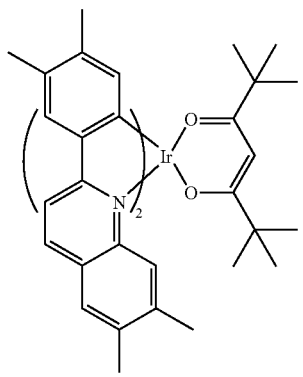

A-76 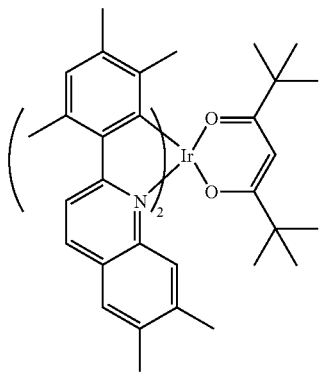

A-77 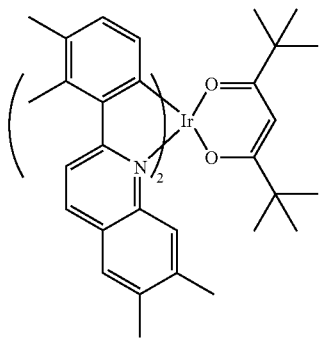

A-78 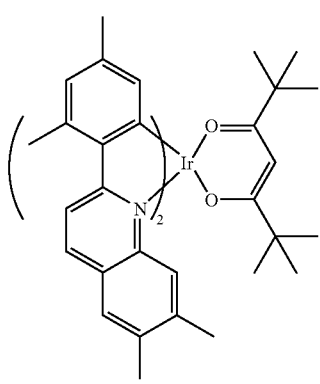

A-79 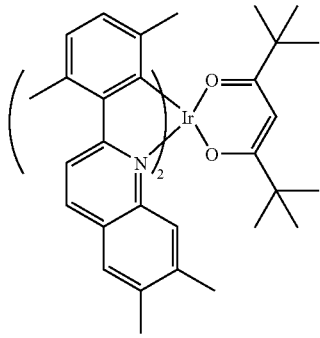

A-80 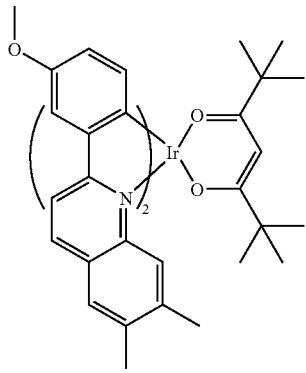

That is, the second embodiment is different from the first embodiment in examples of preferred compounds that can be represented by Formula 1.

The organic electroluminescent (EL) device of the second embodiment has a structure wherein a light-emitting layer is interposed between an anode and a cathode, wherein the red phosphorescent compound of Formula 1 is used as a dopant for the light-emitting layer.

The light-emitting layer may use, as a host, one selected from Al complexes, Zn complexes and carbazole derivatives.

Preferably, the Al and Zn complexes have at least one ligand selected from the group consisting of quinol, biphenyl, isoquinol, phenyl, methylquinol, dimethylquinol and dimethylisoquinol, and the carbazole derivatives include 4,4'-N,N'-dicarbazole biphenyl (CBP).

Preferably, the dopant is used in an amount of 0.1 to 50% by weight.

Hereinafter, a method for synthesizing some phosphorescent compounds used for organic electroluminescent devices according to the second embodiment of the present invention will be given.

Synthesis Example (1) Synthesis of 2-(1-methylphenyl)-6-dimethylquinoline

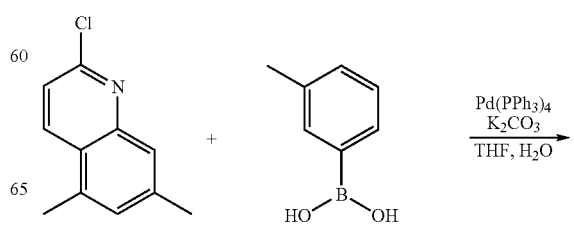

(3) Synthesis of iridium (III) (2-(3-methylphenyl)-5, 7-dimethylquinoline-N,C$^{2'}$) (2,4-pentanedionate-O, O) (A-1)

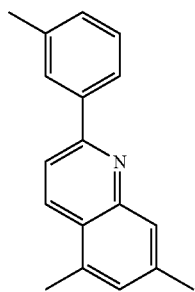

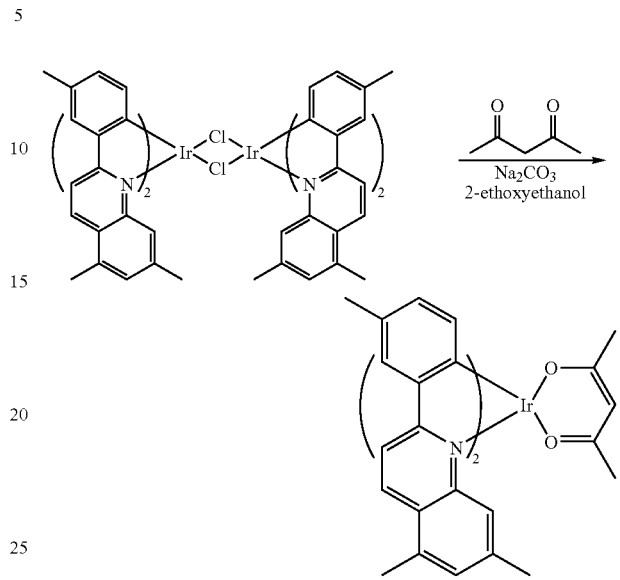

3-methylphenyl borate (13 mmol), 2-chloro-5,7-dimethylquinoline (10 mmol), tetrakis(triphenylphosphine)palladium(0)(0.5 mmol) and potassium carbonate (15 g) are dissolved in tetrahydrofuran (30 ml) and distilled water (10 ml) in a dried two-neck round bottom flask and then stirred at about 100° C. for about 24 hours. After completion of the reaction, the tetrahydrofuran and toluene are removed.

Subsequently, the reaction mixture is extracted with dichloromethane and water, distilled under reduced pressure and purified by silica gel column chromatography.

Then, the solvents are distilled under reduced pressure and recrystallized with dichloromethane and petroleum ether. The resulting solid is filtered to yield the target compound, 2-(3-methylphenyl)-5,7-dimethylquinoline (1.9 g).

(2) Synthesis of Chloro-Crosslinked Dimer Complex

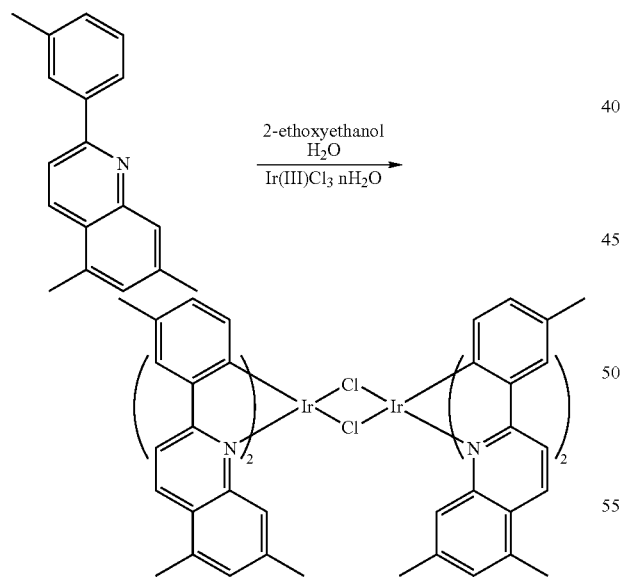

Iridium (III) chloride (5 mmol) and 2-(3-methylphenyl)-5, 7-dimethylquinoline (10 mmol) are added to a mixed solvent (3:1) of 2-ethoxyethanol and distilled water, and then refluxed for about 24 hours.

Then, water is added thereto and the resulting solid is filtered, followed by washing with methanol and petroleum ether to yield the chloro-crosslinked dimer complex.

The chloro-crosslinked dimer complex (1 mmol), 2,4-pentanedione (3 mmol) and sodium carbonate (Na$_2$CO$_3$, 6 mmol) are added to 2-ethoxyethanol (30 mL) and refluxed for about 24 hours.

Then, the reaction mixture is allowed to cool to room temperature and then filtered with addition of distilled water to obtain a solid.

The solid is dissolved in dichloromethane. The solution is filtered through silica gel. The dichloromethane is distilled off under reduced pressure and the residue is washed with methanol and petroleum ether to yield the target compound.

Hereinafter, a detailed description will be made of preferred examples associated with the organic electroluminescent (EL) device according to the present invention.

Figure 3:
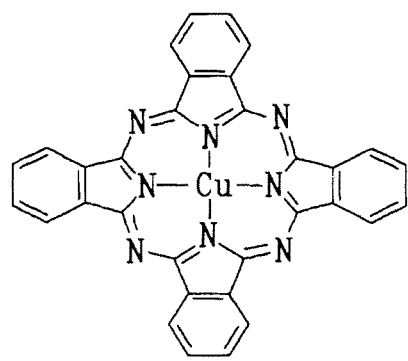
FIG. 3 shows structural formulas of organic compounds used in the second embodiment of the present invention.
Figure 3:
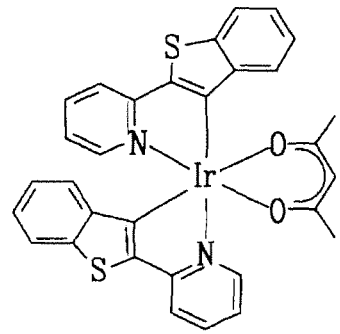
Figure 3:
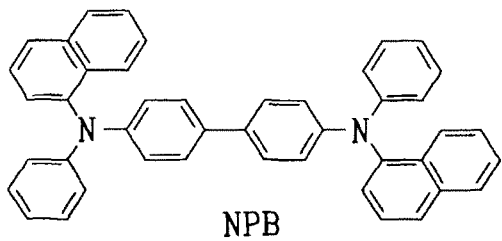
Figure 3:
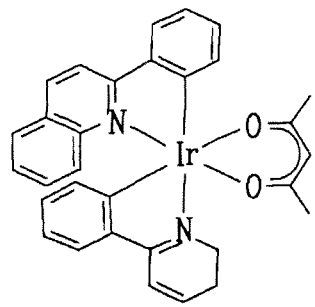
Figure 3:
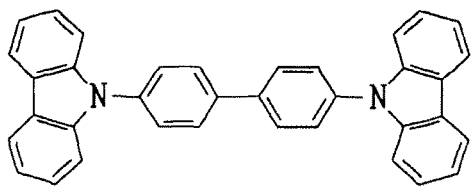
Figure 3:
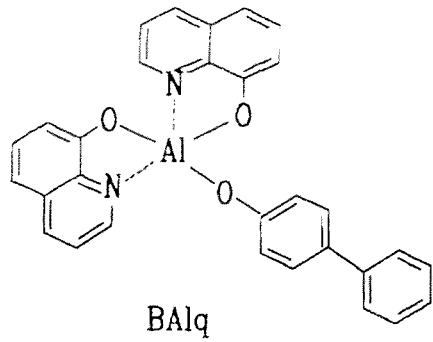
Figure 3:
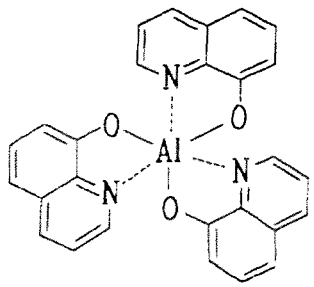

FIG. 3 shows structural formulas of organic compounds used in the second embodiment of the present invention.

EXAMPLES

Example 1

An ITO glass substrate was patterned such that it had a light-emitting area of 3 mm×3 mm, followed by cleaning.

After the patterned substrate was disposed in a vacuum chamber, the base pressure of the chamber was adjusted to 1×10$^{-6}$ torr.

Then, the organic compounds shown in FIG. 3, i.e., CuPc (200 Å), NPB (400 Å), BAlq+A-1 (5%) (200 Å), Alq3 (300 Å), LiF (5 Å) and Al (1,000 Å) were sequentially deposited on the ITO glass substrate to fabricate an organic EL device.

The organic EL device thus fabricated exhibited luminance of about 1,665 cd/m$^2$ and a voltage of 5.6 V at an electric current of about 0.9 mA. At this time, the CIE chromaticity coordinates were x=0.642 and y=0.348.

The lifetime (defined as the time taken before the luminance of the organic EL device decreases to half its initial value) of the organic EL device was about 7,000 hours at about 2,000 cd/m².

Example 2

An ITO glass substrate was patterned such that it had a light-emitting area of 3 mm×3 mm, followed by cleaning.

After the patterned substrate was disposed in a vacuum chamber, the base pressure of the chamber was adjusted to 1×10⁻⁶ torr.

Then, the organic compounds shown in FIG. 3, i.e., CuPc (200 Å), NPB (400 Å), BAlq+A-4 (5%) (200 Å), Alq3 (300 Å), LiF (5 Å) and Al (1,000 Å) were sequentially deposited on the ITO glass substrate to fabricate an organic EL device.

The organic EL device thus fabricated exhibited luminance of about 1,310 cd/m² and a voltage of 5.8 V at an electric current of about 0.9 mA. At this time, the CIE chromaticity coordinates were x=0.657 and y=0.351.

The lifetime (defined as the time taken before the luminance of the organic EL device decreases to half its initial value) of the organic EL device was about 6,500 hours at about 2,000 cd/m².

Example 3

An ITO glass substrate was patterned such that it had a light-emitting area of 3 mm×3 mm, followed by cleaning.

After the patterned substrate was disposed in a vacuum chamber, the base pressure of the chamber was adjusted to 1×10⁻⁶ torr.

Then, the organic compounds shown in FIG. 3, i.e., CuPc (200 Å), NPB (400 Å), BAlq+A-17 (5%) (200 Å), Alq3 (300 Å), LiF (5 Å) and Al (1,000 Å) were sequentially deposited on the ITO glass substrate to fabricate an organic EL device.

The organic EL device thus fabricated exhibited luminance of about 1,715 cd/m² and a voltage of 5.7 V at an electric current of about 0.9 mA. At this time, the CIE chromaticity coordinates were x=0.640 and y=0.349.

The lifetime (defined as the time taken before the luminance of the organic EL device decreases to half its initial value) of the organic EL device was about 7,500 hours at about 2,000 cd/m².

Example 4

An ITO glass substrate was patterned such that it had a light-emitting area of 3 mm×3 mm, followed by cleaning.

After the patterned substrate was disposed in a vacuum chamber, the base pressure of the chamber was adjusted to 1×10⁻⁶ torr.

Then, the organic compounds shown in FIG. 3, i.e., CuPc (200 Å), NPB (400 Å), BAlq+A-67 (5%) (200 Å), Alq3 (300 Å), LiF (5 Å) and Al (1,000 Å) were sequentially deposited on the ITO glass substrate to fabricate an organic EL device.

The organic EL device thus fabricated exhibited luminance of about 1,741 cd/m² and a voltage of 5.9 V at an electric current of about 0.9 mA. At this time, the CIE chromaticity coordinates were x=0.648 and y=0.330.

The lifetime (defined as the time taken before the luminance of the organic EL device decreases to half its initial value) of the organic EL device was about 7,000 hours at about 2,000 cd/m².

Comparative Example 1

An ITO glass substrate was patterned such that it had a light-emitting area of 3 mm×3 mm, followed by cleaning.

After the patterned substrate was disposed in a vacuum chamber, the base pressure of the chamber was adjusted to 1×10⁻⁶ torr.

Then, the organic compounds shown in FIG. 3, i.e., CuPc (200 Å), NPB (400 Å), BAlq+RD1 (7%) (200 Å), Alq3 (300 Å), LiF (5 Å) and Al (1,000 Å) were sequentially deposited on the ITO glass substrate to fabricate an organic EL device.

The organic EL device thus fabricated exhibited luminance of about 780 cd/m² and a voltage of 7.5 V at an electric current of about 0.9 mA. At this time, the CIE chromaticity coordinates were x=0.659 and y=0.329.

The lifetime (defined as the time taken before the luminance of the organic EL device decreases to half its initial value) of the organic EL device was about 2,500 hours at about 2,000 cd/m².

Comparative Example 2

An ITO glass substrate was patterned such that it had a light-emitting area of 3 mm×3 mm, followed by cleaning.

After the patterned substrate was disposed in a vacuum chamber, the base pressure of the chamber was adjusted to 1×10⁻⁶ torr.

Then, the organic compounds shown in FIG. 3, i.e., CuPc (200 Å), NPB (400 Å), BAlq+RD2 (7%) (200 Å), Alq3 (300 Å), LiF (5 Å) and Al (1,000 Å) were sequentially deposited on the ITO glass substrate to fabricate an organic EL device.

The organic EL device thus fabricated exhibited a luminance of about 1,173 cd/m² and a voltage of 6.0 V at an electric current of about 0.9 mA. At this time, the CIE chromaticity coordinates were x=0.606 and y=0.375.

The lifetime (defined as the time taken before the luminance of the organic EL device decreases to half its initial value) of the organic EL device was about 4,000 hours at about 2,000 cd/m².

The organic EL devices fabricated in the Examples and Comparative Example were evaluated for efficiency, CIE chromaticity coordinates, luminance and lifetime properties. The results are shown in Table 2.

TABLE 2

| Device | Voltage (V) | Electric current (mA) | Luminance (cd/m²) | Current efficiency (cd/A) | Power efficiency (lm/W) | Quantum efficiency (%) | CIE (X) | CIE (Y) | Life time (h) (half the initial luminance) |
|---|---|---|---|---|---|---|---|---|---|
| Ex. 1 | 5.6 | 0.9 | 1694 | 16.94 | 9.5 | 17% | 0.642 | 0.348 | 7000 |
| Ex. 2 | 5.8 | 0.9 | 1310 | 13.10 | 7.1 | 16% | 0.657 | 0.351 | 6500 |
| Ex. 3 | 5.7 | 0.9 | 1715 | 17.15 | 9.4 | 18% | 0.640 | 0.349 | 7500 |
| Ex. 4 | 5.9 | 0.9 | 1742 | 17.42 | 9.3 | 19% | 0.648 | 0.330 | 7000 |
| Comp. Ex. 1 | 7.5 | 0.9 | 780 | 7.80 | 3.3 | 10% | 0.659 | 0.329 | 2500 |
| Comp. Ex. 2 | 6.0 | 0.9 | 1173 | 11.73 | 6.2 | 12% | 0.606 | 0.375 | 4000 |

As can be seen from Table 2 above, the organic EL devices of the present invention exhibits an operation voltage of at least about 6.0 V or less, a luminance of at least about 1,300 cd/m² or higher, and a lifetime of about 6,500 hours or longer.

As apparent from the foregoing, the organic electroluminescent (EL) device according to the present invention employs the red phosphorescent compound of Formula 1 as a dopant for the light-emitting layer, thus exhibiting excellent color purity, high luminescence efficiency, and long luminescence lifetime.

It will be apparent to those skilled in the art that various modifications and variations can be made in the present invention without departing from the spirit or scope of the inventions. Thus it is intended that the present invention covers the modifications and variations of this invention provided they come within the scope of the appended claims and their equivalents.

What is claimed is:

1. A red phosphorescent compound represented by Formula 1 below:

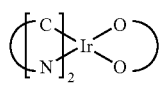 (1)

wherein

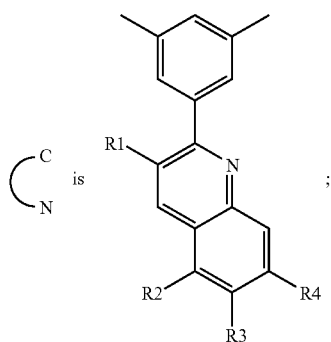

R1, R2, R3 and R4 are each independently selected from the group consisting of hydrogen, substituted or unsubstituted $C_1$-$C_6$ alkyl, substituted or unsubstituted $C_1$-$C_6$ alkoxy and combinations thereof, in which at least two of R1, R2, R3 and R4 are each independently selected from the group consisting of substituted or unsubstituted $C_1$-$C_6$ alkyl, substituted or unsubstituted $C_1$-$C_6$ alkoxy and combinations thereof, or each of R1, R2, R3 and R4 is halogen;

when each of R1, R2 and R4 is $C_1$-$C_6$ alkyl, R3 is selected from the group consisting of substituted or unsubstituted $C_1$-$C_6$ alkyl, substituted or unsubstituted $C_1$-$C_6$ alkoxy and combinations thereof;

when each of R1 and R3 is $C_1$-$C_6$ alkyl or $C_1$-$C_6$ alkoxy, R2 or R4 is selected from the group consisting of substituted or unsubstituted $C_1$-$C_6$ alkoxy and combinations thereof; and when each of R1 and R4 is $C_1$-$C_6$ alkyl or $C_1$-$C_6$ alkoxy, R2 or R3 is selected from the group consisting of substituted or unsubstituted $C_1$-$C_6$ alkyl, substituted or unsubstituted $C_1$-$C_6$ alkoxy and combinations thereof;

is selected from 2,4-pentanedione

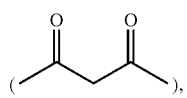

2,2,6,6-tetramethylheptane-3,5-dione

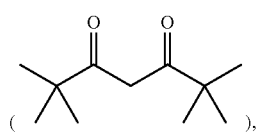

1,3-propanedione

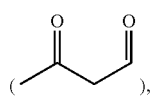

1,3-butanedione

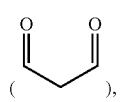

3,5-heptanedione,

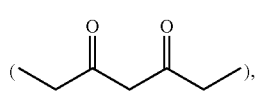

1,1,1-trifluoro-2,4-pentanedione

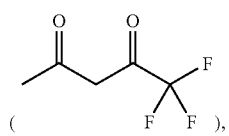

1,1,1,5,5,5-hexafluoro-2,4-pentanedione

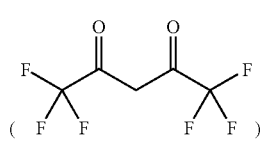 [SMILES: O=C(CC(=O)C(F)(F)F)C(F)(F)F]

and 2,2-dimethyl-3,5-hexanedione

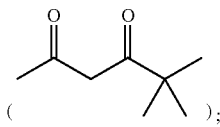

and when

is 2,4-pentanedione

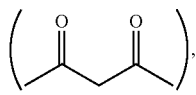

at least one of R1, R2, R3 and R4 is not hydrogen, methyl, methoxyl, or fluoro.

2. The red phosphorescent compound according to claim 1, wherein the $C_1$-$C_6$ alkyl is selected from the group consisting of methyl, ethyl, n-propyl, i-propyl, n-butyl, butyl and t-butyl.

3. The red phosphorescent compound according to claim 1, wherein the $C_1$-$C_6$ alkoxy is selected from the group consisting of methoxy, ethoxy, n-propoxy, i-propoxy, n-butoxy, i-butoxy and t-butoxy.

4. The red phosphorescent compound according to claim 1, wherein

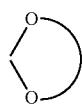

is selected from 2,2,6,6-tetramethylheptane-3,5-dione

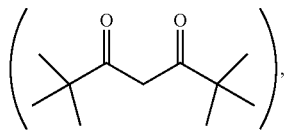

1,3-propanedione

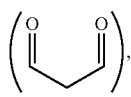

1,3-butanedione

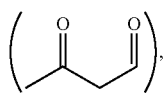

3,5-heptanedione

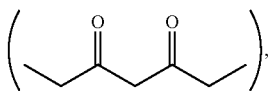

1,1,1-trifluoro-2,4-pentanedione

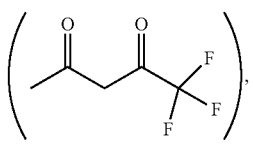

1,1,1,5,5,5-hexafluoro-2,4-pentanedione

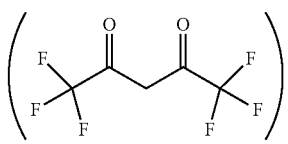

and 2,2-dimethyl-3,5-hexanedione

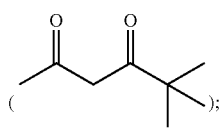

and

is selected from the following compounds:

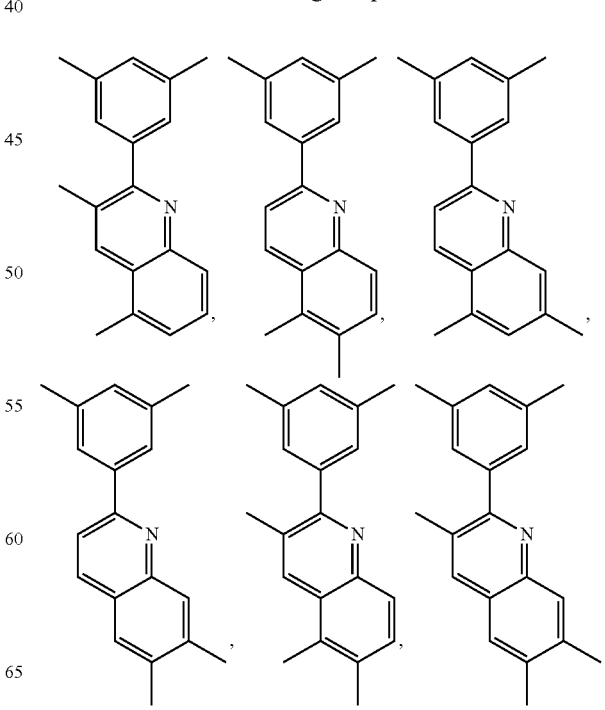

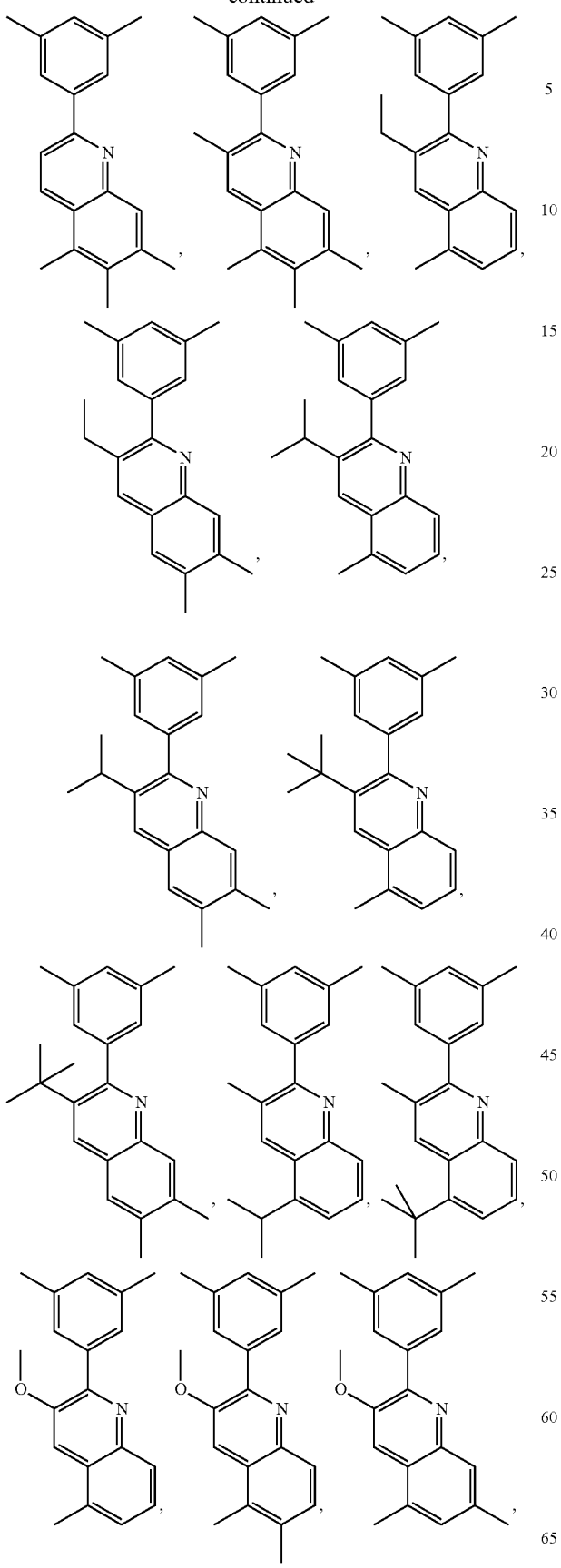
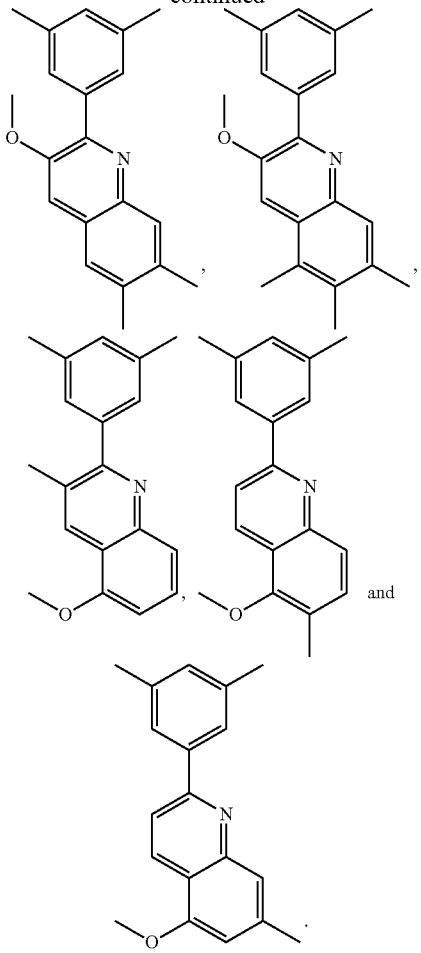
5. The red phosphorescent compound according to claim 1, wherein the compound of Formula 1 is selected from the following compounds:
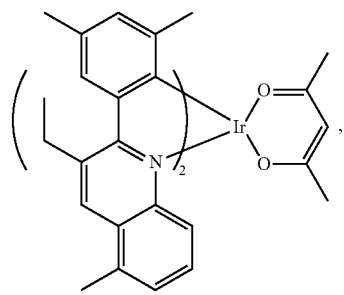
A-12
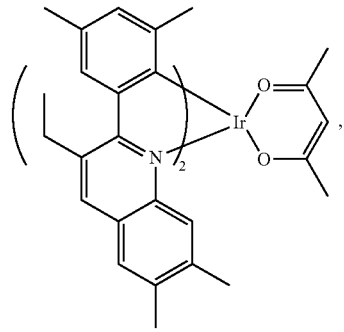
A-15

A-17 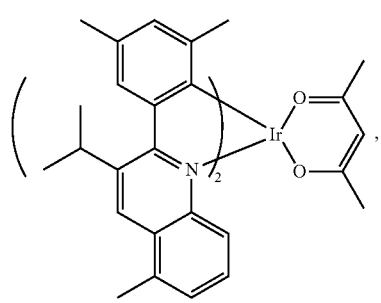
A-20 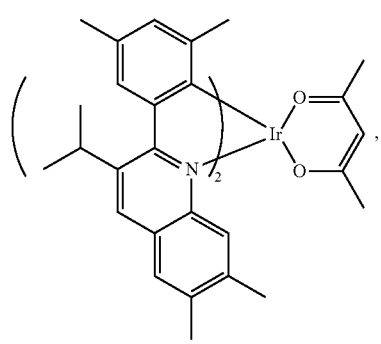
A-21 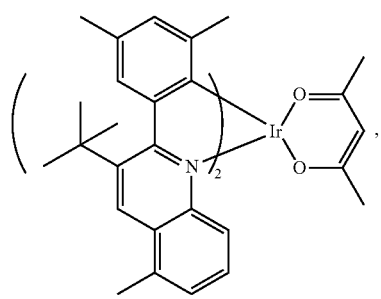
A-24 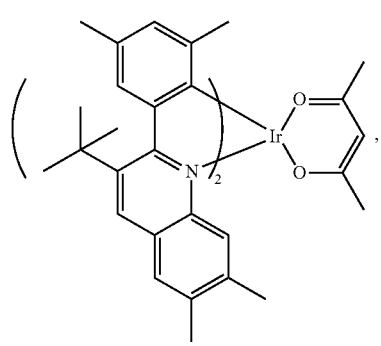
A-25 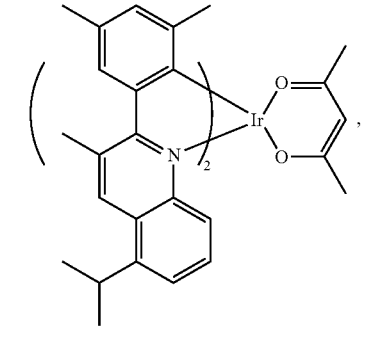
A-26 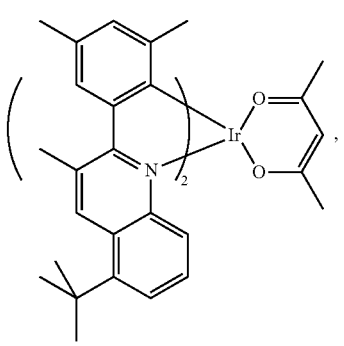
B-1 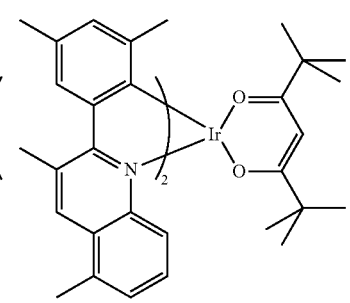
B-4 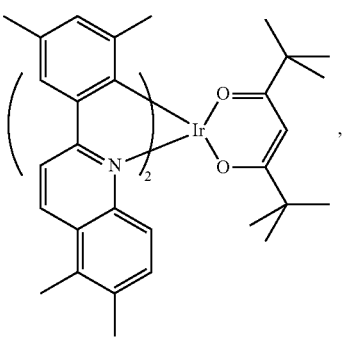
B-5 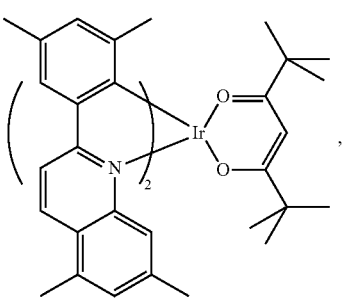
B-6 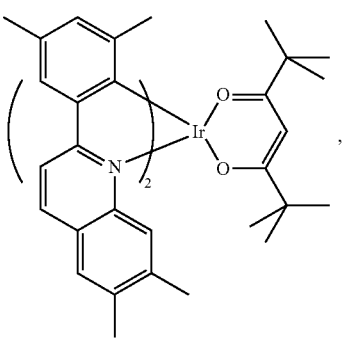

-continued
B-7
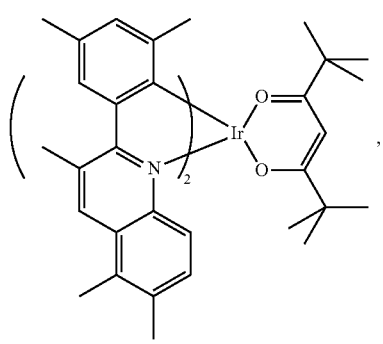
B-9
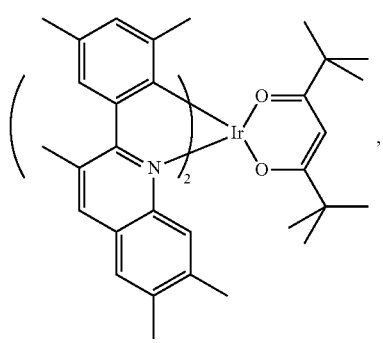
B-10
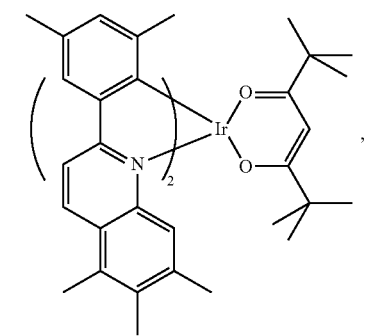
B-11
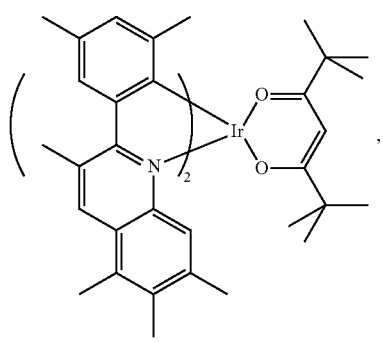
B-12
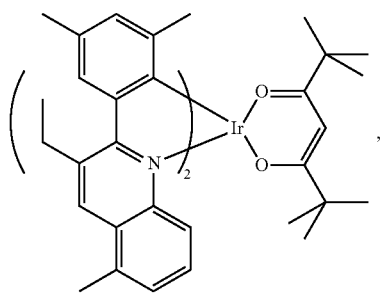
-continued
B-15
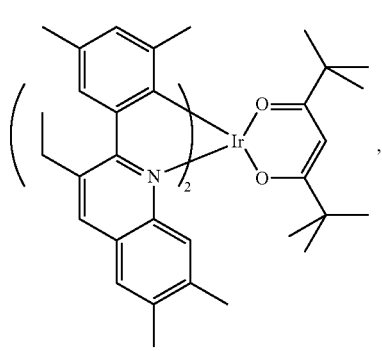
B-17
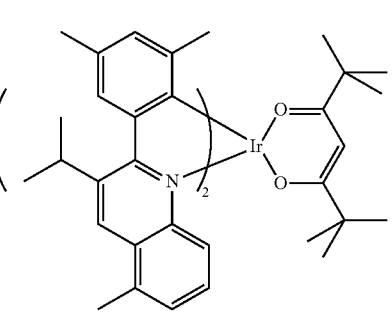
B-20
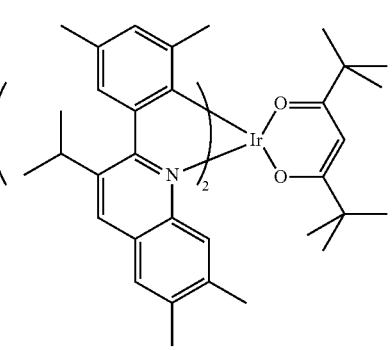
B-21
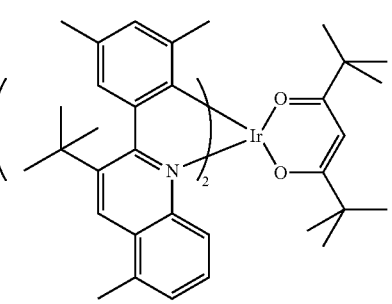
B-24
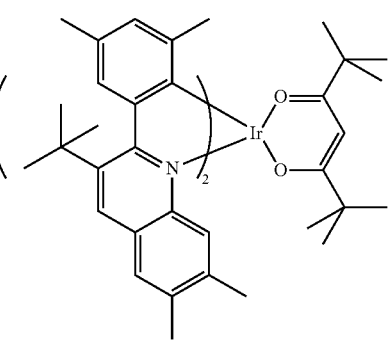

B-25 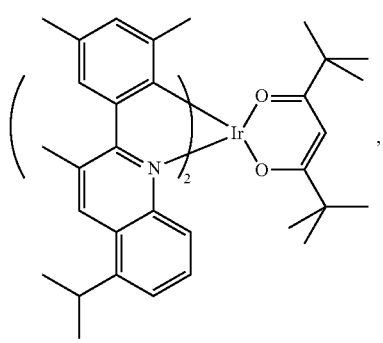
B-26 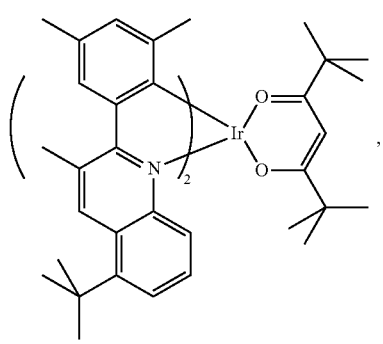
B-29 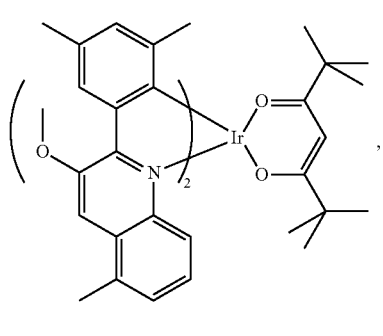
B-32 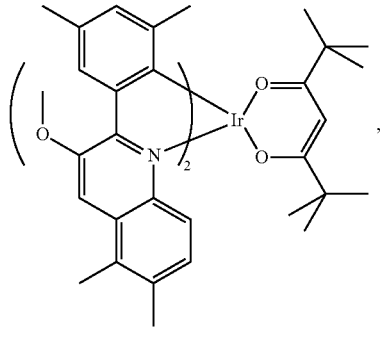
B-33 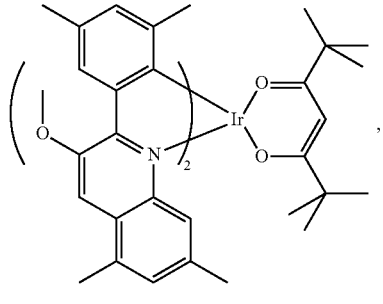
B-34 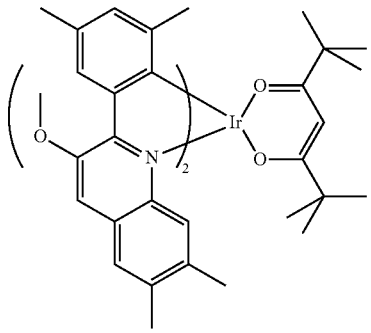
B-35 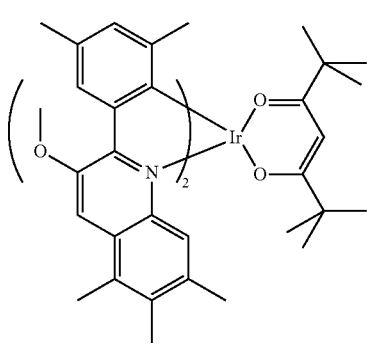
B-39 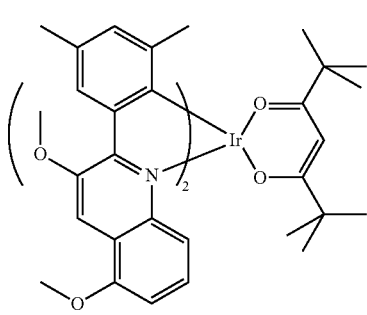
B-40 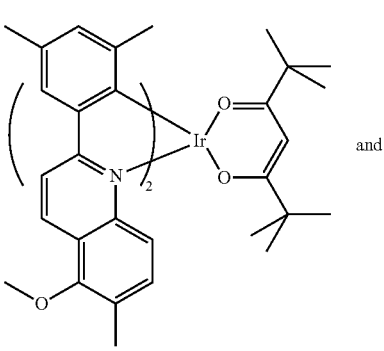
and
B-41 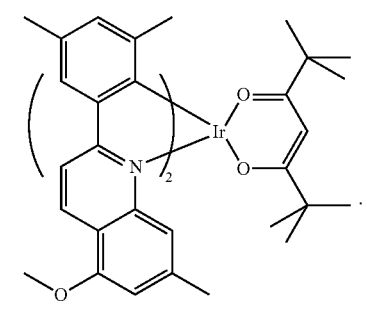

6. The red phosphorescent compound according to claim 1, wherein each of R1, R2, R3 and R4 is halogen selected from the group consisting of F, Cl and Br.

7. The red phosphorescent compound according to claim 1, wherein each of R1, R2, R3 and R4 is independently selected from the group consisting of ethyl, n-propyl, i-propyl, n-butyl, i-butyl, t-butyl, ethoxy, n-propoxy, i-propoxy, n-butoxy, i-butoxy and t-butoxy.

8. The red phosphorescent compound according to claim 1, wherein

is selected from the following compounds:

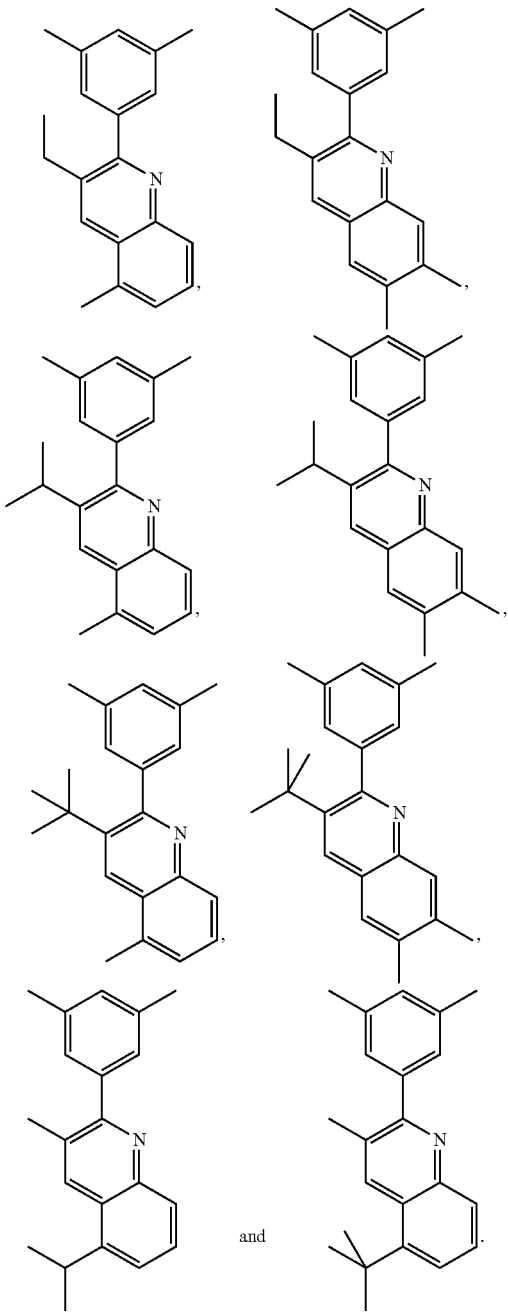

and

9. The red phosphorescent compound according to claim 1, wherein R3 is selected from the group consisting of substituted or unsubstituted $C_1$-$C_6$ alkyl, substituted or unsubstituted $C_1$-$C_6$ alkoxy and combinations thereof.

10. The red phosphorescent compound according to claim 1, wherein

R3 is selected from the group consisting of substituted or unsubstituted $C_1$-$C_6$ alkyl, substituted or unsubstituted $C_1$-$C_6$ alkoxy and combinations thereof, and at least two of R1, R2 and R4 are each independently selected from the group consisting of substituted or unsubstituted $C_1$-$C_6$ alkyl, substituted or unsubstituted $C_1$-$C_6$ alkoxy and combinations thereof.

11. The red phosphorescent compound according to claim 1, wherein at least one of R1, R2, R3 and R4 is not hydrogen, methyl, methoxyl, or fluoro.

12. The red phosphorescent compound according to claim 1, wherein when

is 2,4-pentanedione

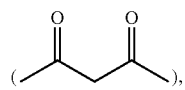

at least one of R1, R2, R3 and R4 is not hydrogen, methyl, methoxyl or F.

13. The red phosphorescent compound according to claim 1, wherein when

is 2,4-pentanedione

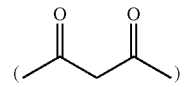

or 1,1,1,5,5,5-hexafluoro-2,4-pentanedione

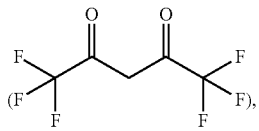

at least one of R1, R2, R3 and R4 is not hydrogen, methyl, methoxyl, or fluoro.

14. A red phosphorescent compound represented by Formula 2 below:

(2)

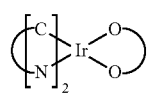

wherein

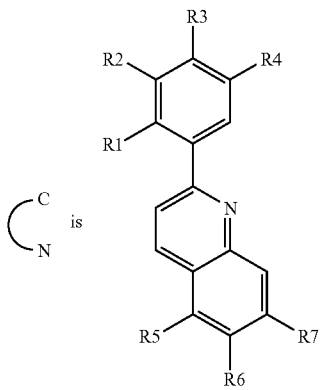

is wherein R1, R2, R3 and R4 are each independently selected from the group consisting of hydrogen, $C_1$-$C_6$ alkyl and $C_1$-$C_4$ alkoxy, in which at least one of R1, R2, R3 and R4 is $C_1$-$C_6$ alkyl or $C_1$-$C_4$ alkoxy;

R5, R6 and R7 are each independently selected from hydrogen, $C_1$-$C_6$ alkyl, $C_1$-$C_4$ alkoxy, and combinations thereof, in which at least two of R5, R6 and R7 are each independently selected from the group consisting of $C_1$-$C_6$ alkyl, $C_1$-$C_4$ alkoxy, and combinations thereof;

is selected from 2,4-pentanedione

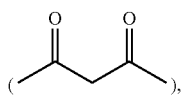

2,2,6,6-tetramethylheptane-3,5-dione

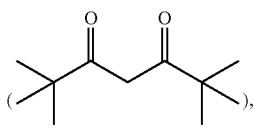

1,3-propanedione

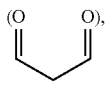

1,3-butanedione

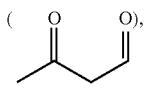

3,5-heptanedione

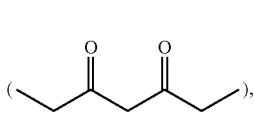

1,1,1-trifluoro-2,4-pentanedione

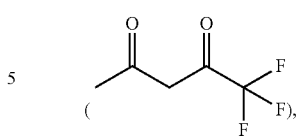

1,1,1,5,5,5-hexafluoro-2,4-pentanedione

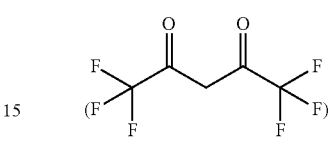

and 2,2-dimethyl-3,5-hexanedione

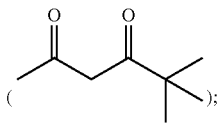

and when

is 2,4-pentanedione

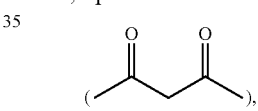

at least one of R1, R2, R3, R4, R5, R6 and R7 is not hydrogen, methyl or methoxy.

15. The red phosphorescent compound according to claim 14, wherein the $C_1$-$C_6$ alkyl is selected from the group consisting of methyl, ethyl, n-propyl, propyl, n-butyl, i-butyl and t-butyl, and the $C_1$-$C_4$ alkoxy is selected from the group consisting of methoxy, ethoxy, n-propoxy, i-propoxy, n-butoxy, i-butoxy and t-butoxy.

16. The red phosphorescent compound according to claim 14, wherein

is selected from 2,2,6,6-tetramethylheptane-3,5-dione

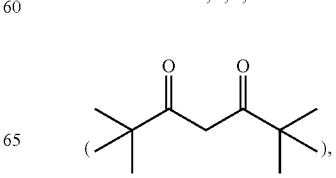

1,3-propanedione
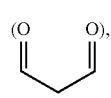
1,3-butanedione
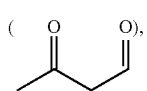
3,5-heptanedione
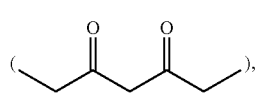
1,1,1-trifluoro-2,4-pentanedione
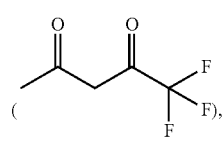
1,1,1,5,5,5-hexafluoro-2,4-pentanedione
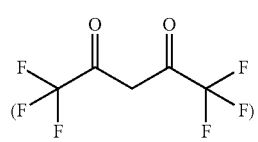
and 2,2-dimethyl-3,5-hexanedione
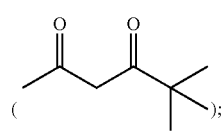
and
is selected from the following compounds:
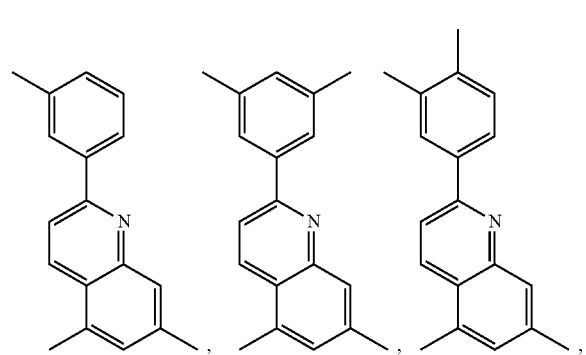
-continued
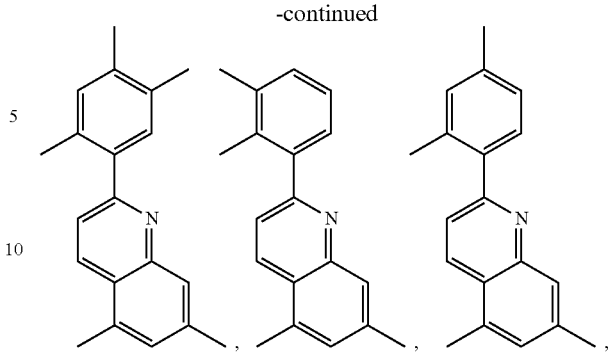
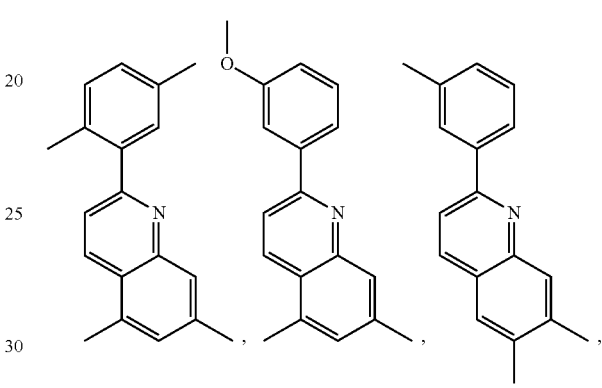
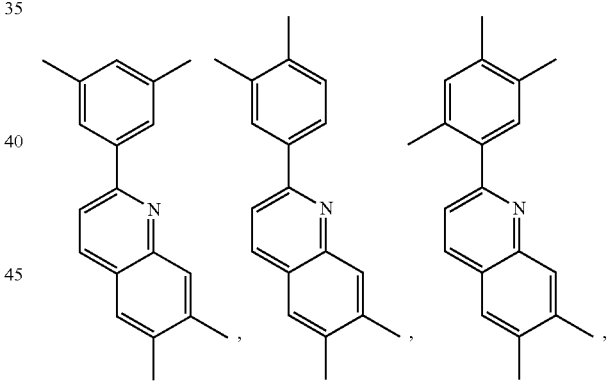
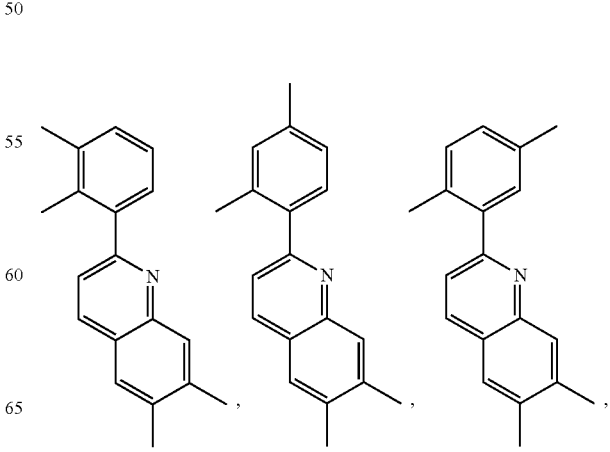

85
-continued
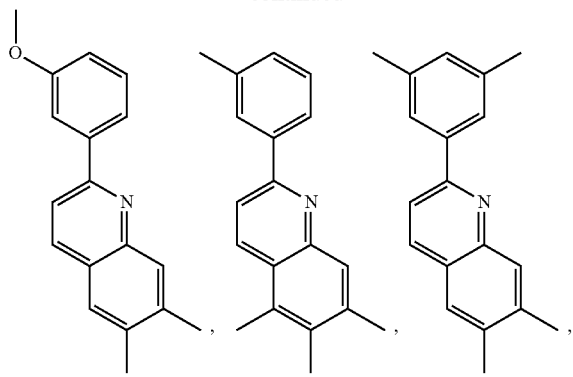
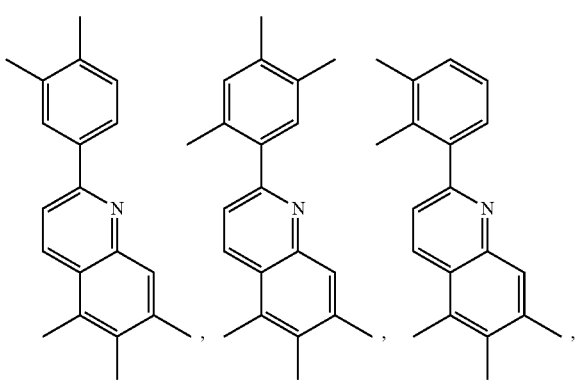
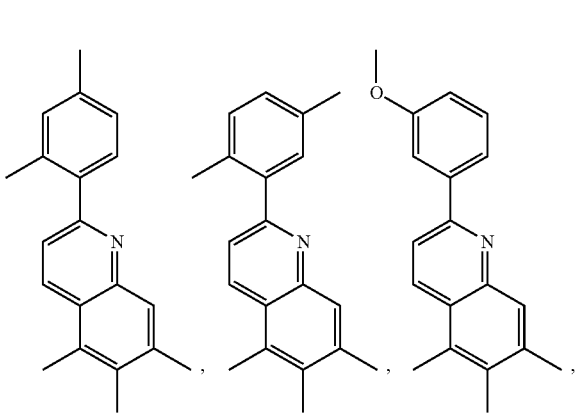
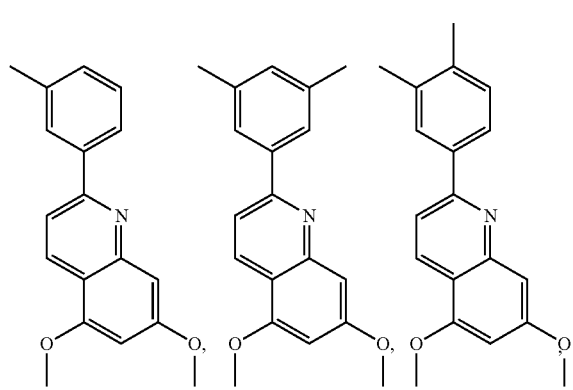
86
-continued
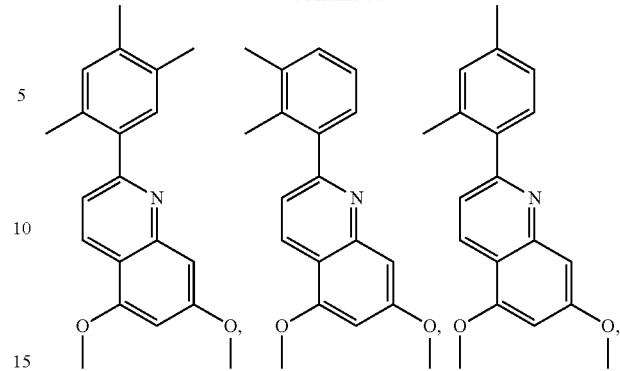
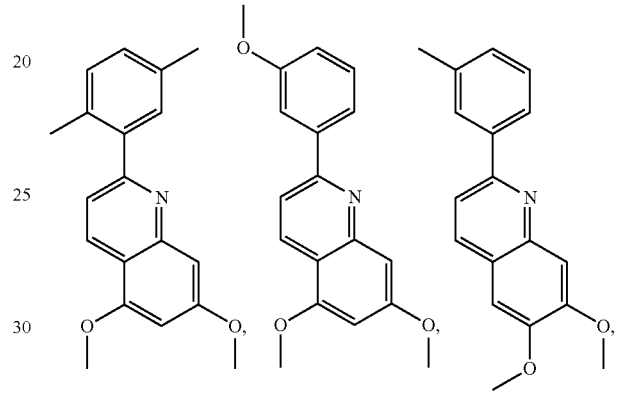
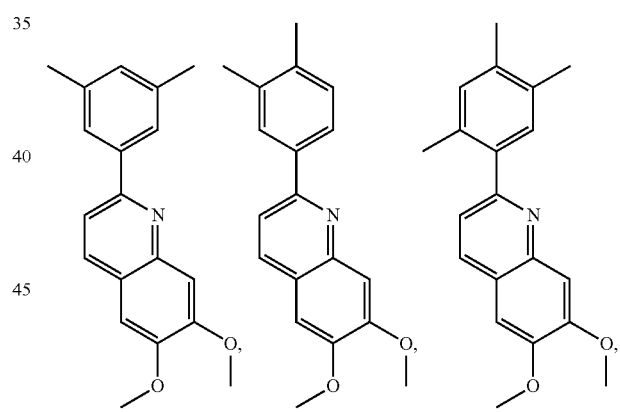
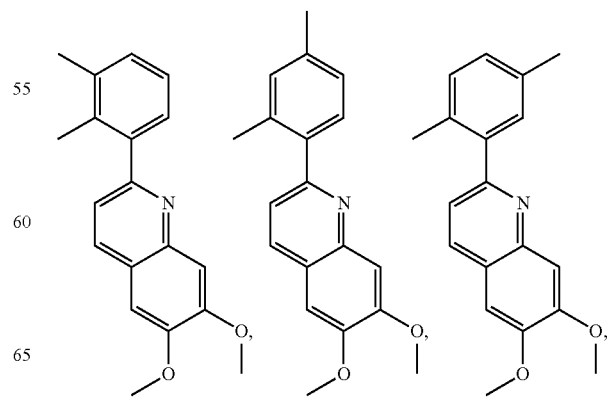

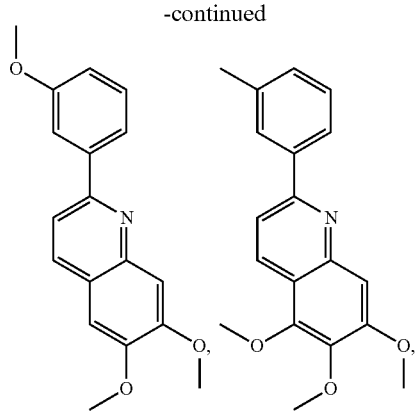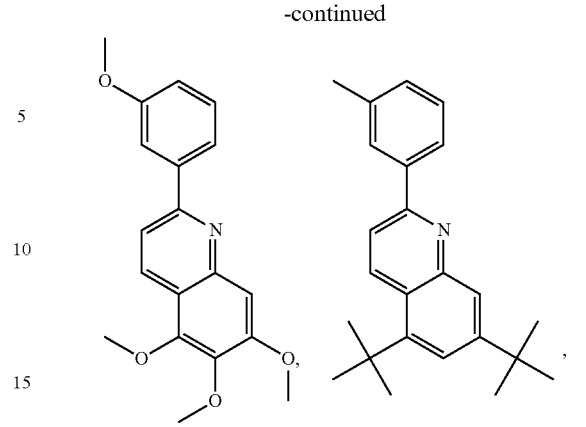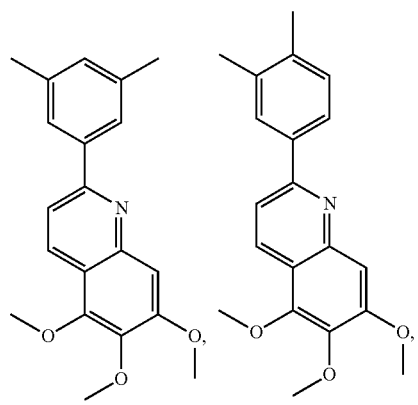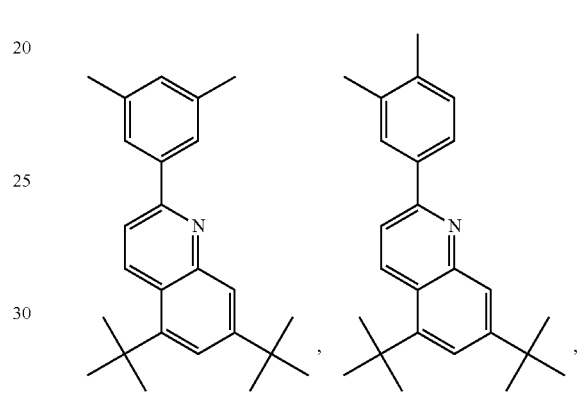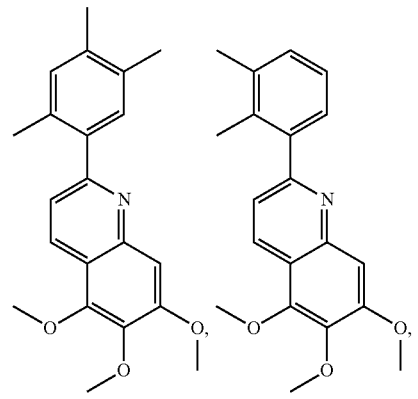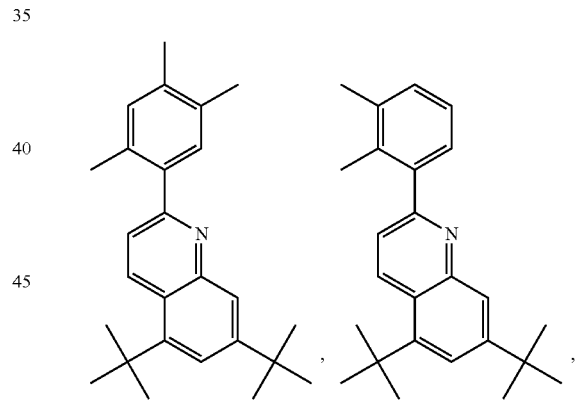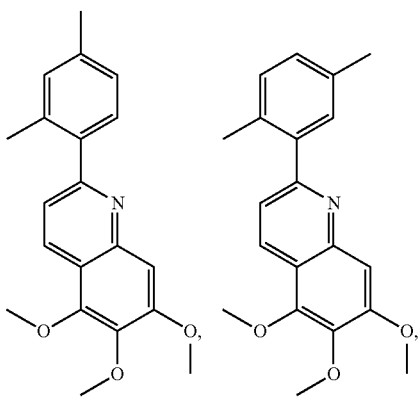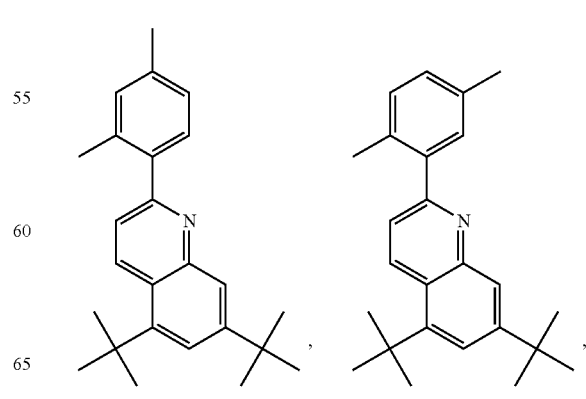

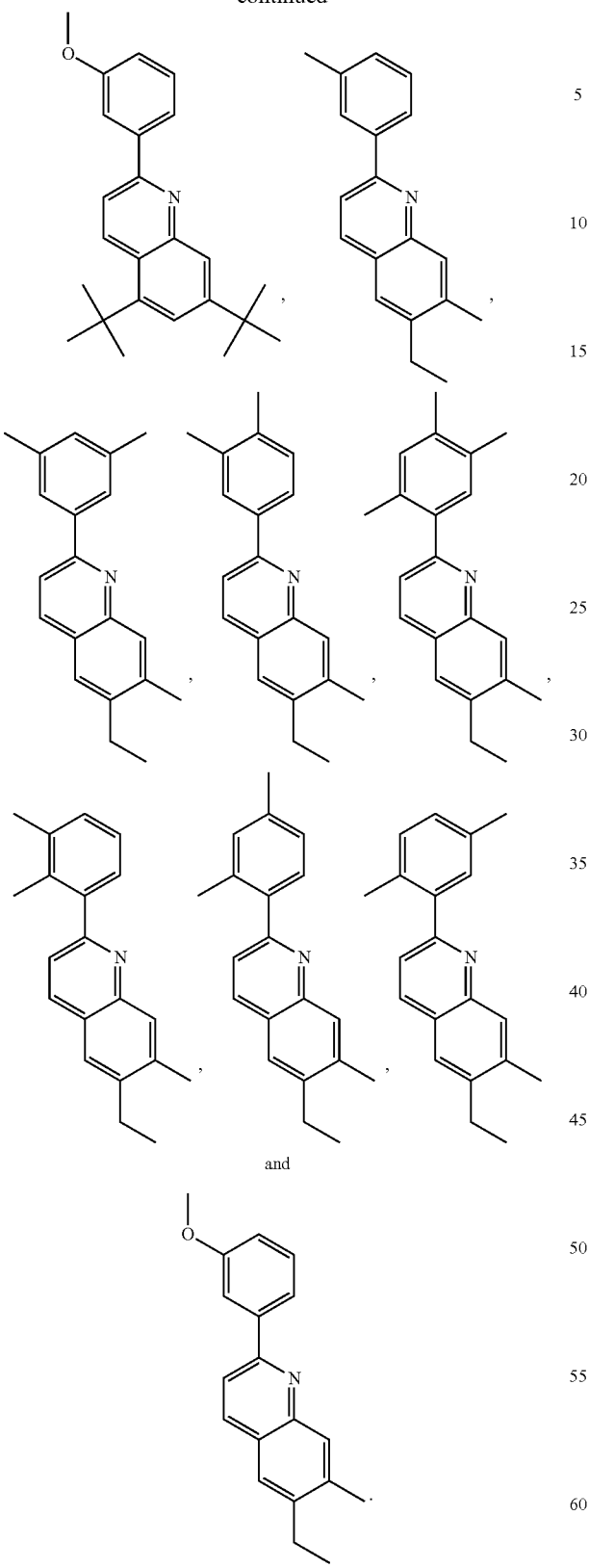
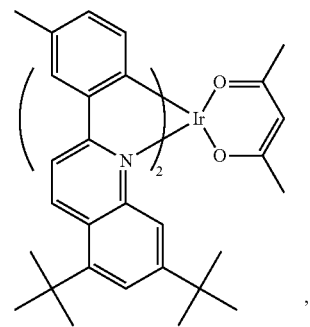
A-49
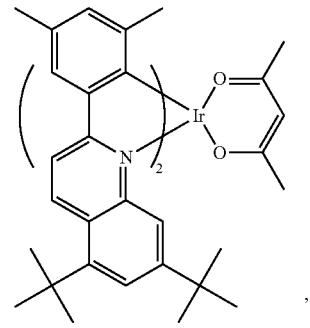
A-50
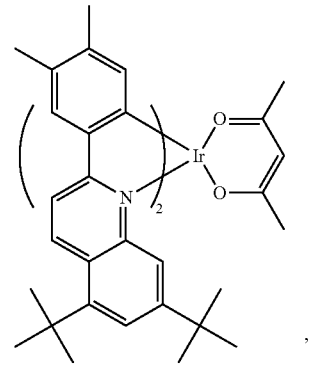
A-51
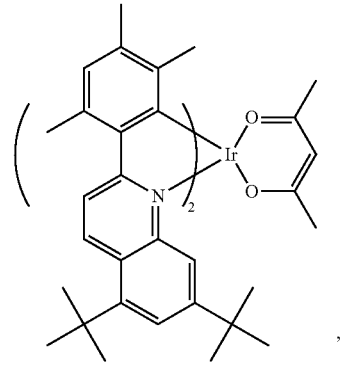
A-52
17. The red phosphorescent compound according to claim 14, wherein the compound of Formula 1 is selected from the following compounds:

A-53
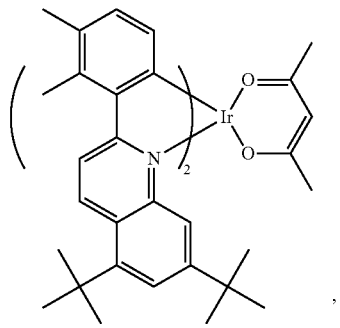
A-54
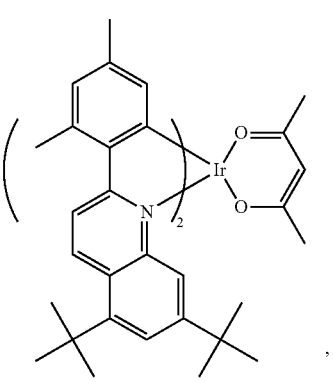
A-55
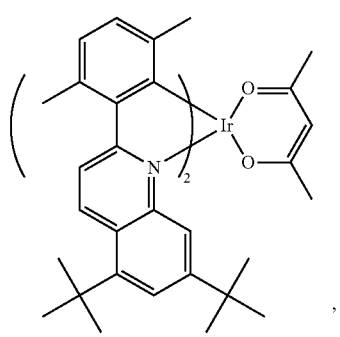
A-56
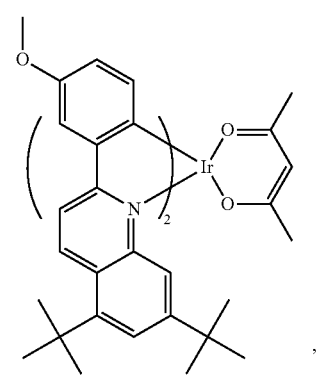
A-57
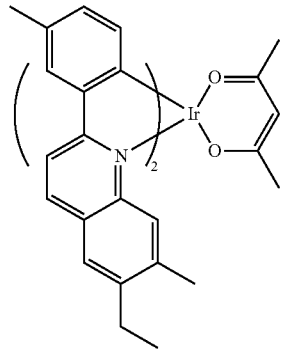
A-58
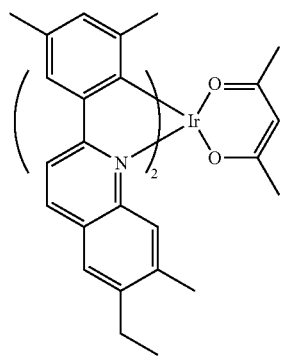
A-59
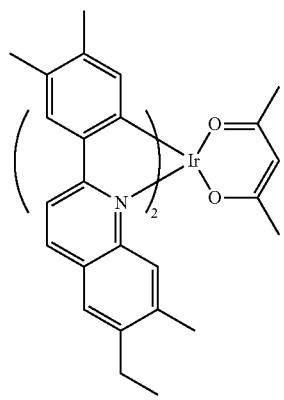
A-60
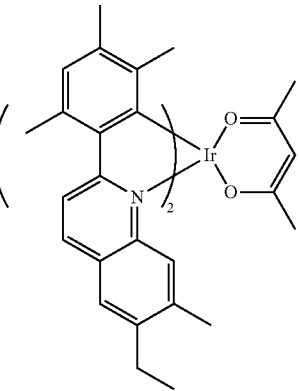

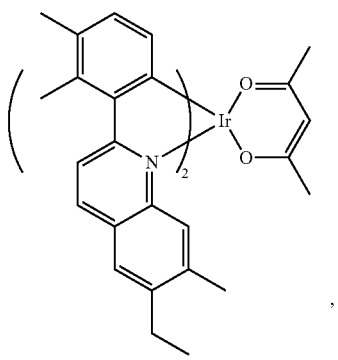
A-61
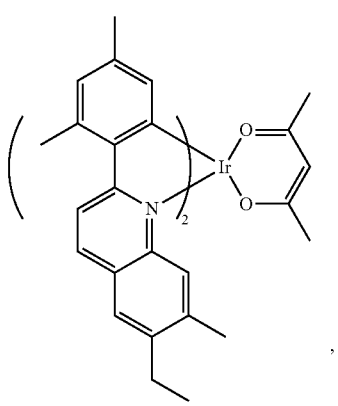
A-62
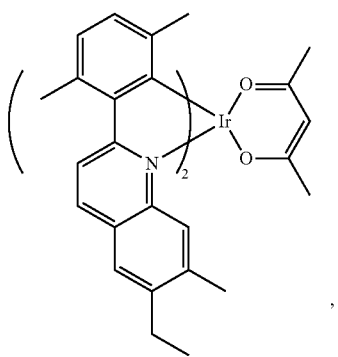
A-63
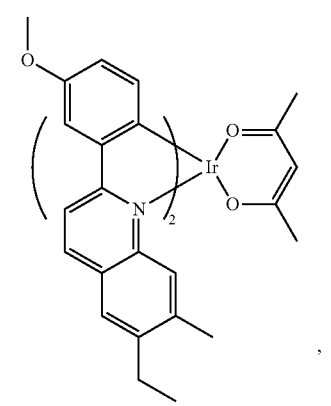
A-64
A-65
A-66
A-67
A-68
A-69

-continued
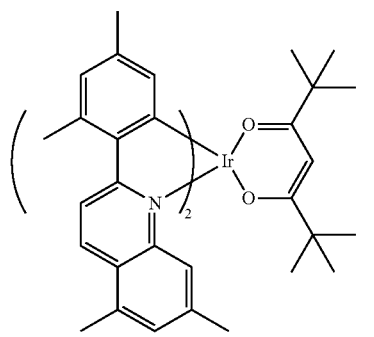
A-70
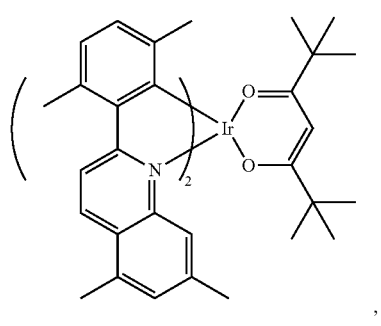
A-71
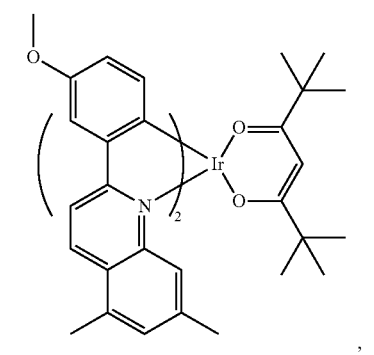
A-72
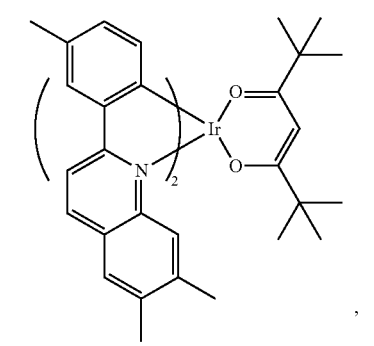
A-73
-continued
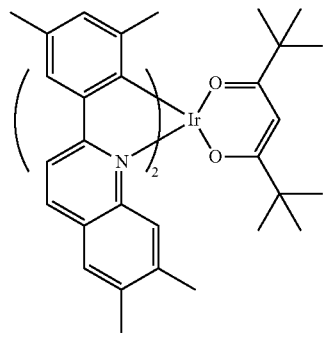
A-74
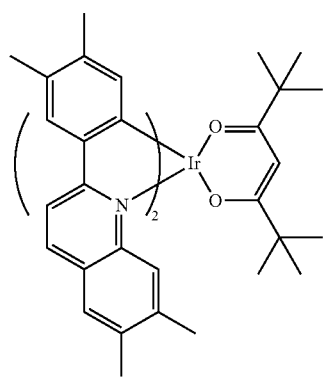
A-75
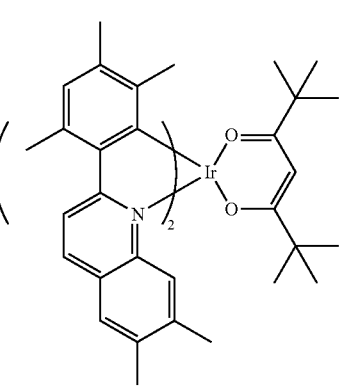
A-76
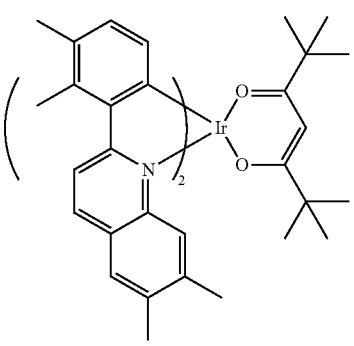
A-77

-continued
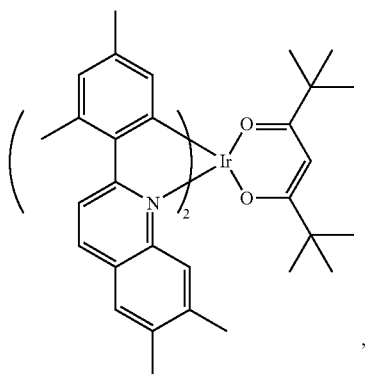
A-78
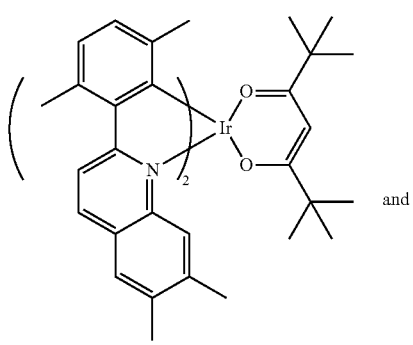
A-79
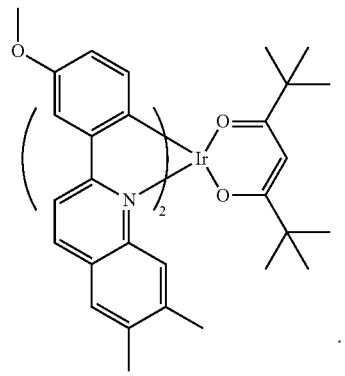
A-80
18. The red phosphorescent compound according to claim 14, wherein
is selected from the following compounds:
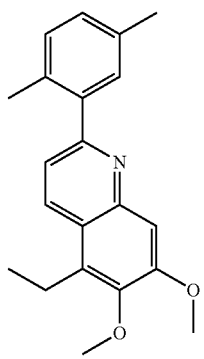 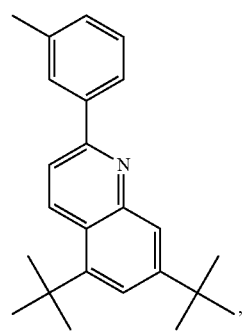
-continued
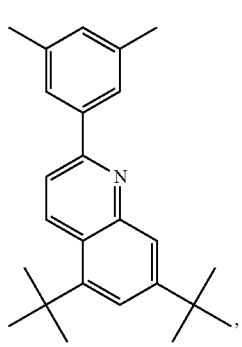 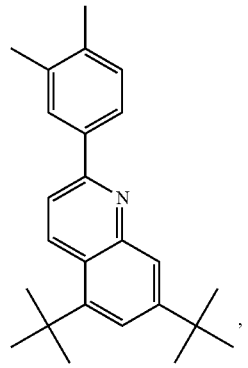
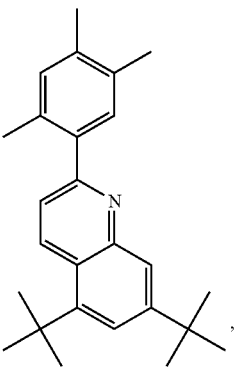 , ,
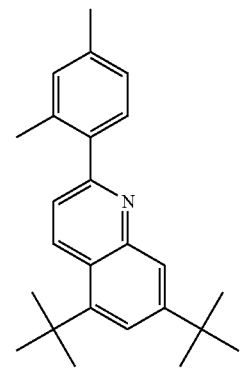 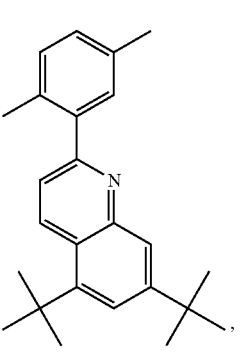
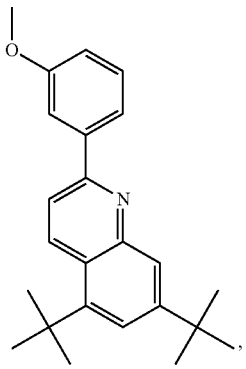 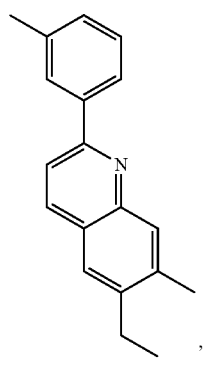

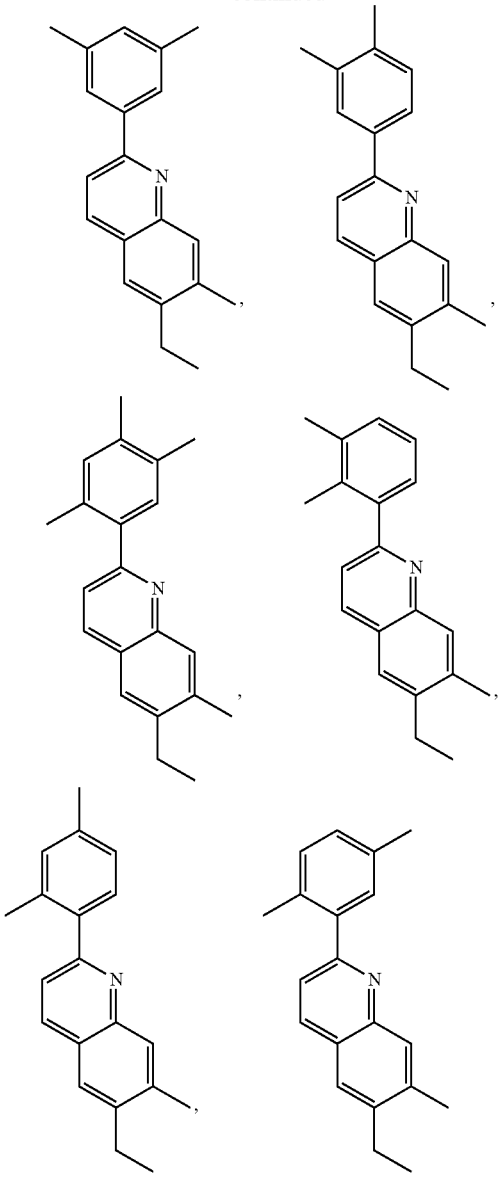

and

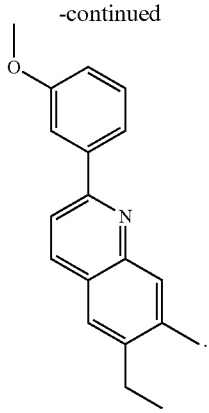

19. An organic electroluminescent (EL) device comprising a light-emitting layer interposed between an anode electrode and a cathode electrode wherein the compound according to any one of claims 1-5, 14, 15, 16 & 17 is used as a dopant for the light-emitting layer.

20. The organic electroluminescent (EL) device according to claim 19, wherein the light-emitting layer uses, as a host, one selected from an Al complex, a Zn complex and a carbazole derivative.

21. The organic electroluminescent (EL) device according to claim 20, wherein the Al or Zn complex has at least one ligand selected from quinol, biphenyl, isoquinol, phenyl, methylquinol, dimethylquinol and dimethylisoquinol, and the carbazole derivative is 4,4'-N,N'-dicarbazole biphenyl (CBP).

22. The organic electroluminescent (EL) device according to claim 19, wherein the dopant is used in an amount of 0.1 to 50% by weight.

23. The organic electroluminescent (EL) device according to claim 19, wherein the organic EL device exhibits an operation voltage of at least 6.0 V or less, a luminance of at least 1,300 cd/m$^2$ or higher, and a lifetime of about 6,500 hours or longer.

* * * * *